United States Patent
Narayan et al.

(10) Patent No.: US 10,398,326 B2
(45) Date of Patent: Sep. 3, 2019

(54) SYSTEM AND METHOD OF IDENTIFYING SOURCES ASSOCIATED WITH BIOLOGICAL RHYTHM DISORDERS

(71) Applicants: The Regents of the University of California, Oakland, CA (US); Topera, Inc., Menlo Park, CA (US)

(72) Inventors: Sanjiv Narayan, La Jolla, CA (US); Carey Robert Briggs, La Jolla, CA (US); Ruchir Sehra, Scottsdale, AZ (US)

(73) Assignees: THE REGENTS OF THE UNIVERSITY OF CALIFORNIA, Oakland, CA (US); THE UNITED STATES OF AMERICA AS REPRESENTED BY THE DEPARTMENT OF VETERANS AFFAIRE, Washington, DC (US); TOPERA, INC., Menlo Park, CA (US)

( * ) Notice: Subject to any disclaimer, the term of this patent is extended or adjusted under 35 U.S.C. 154(b) by 627 days.

(21) Appl. No.: 14/473,990

(22) Filed: Aug. 29, 2014

(65) Prior Publication Data

US 2014/0371609 A1 Dec. 18, 2014

Related U.S. Application Data

(63) Continuation-in-part of application No. 13/844,562, filed on Mar. 15, 2013, now Pat. No. 9,332,915.

(Continued)

(51) Int. Cl.
*A61B 5/024* (2006.01)
*A61B 18/12* (2006.01)
(Continued)

(52) U.S. Cl.
CPC ........ *A61B 5/02405* (2013.01); *A61B 5/0006* (2013.01); *A61B 5/0422* (2013.01);
(Continued)

(58) Field of Classification Search
CPC .................................................... A61B 5/0452
See application file for complete search history.

(56) References Cited

U.S. PATENT DOCUMENTS 4,421,114 A 12/1983 Berkovits et al.
4,630,204 A 12/1986 Mortara
(Continued)

FOREIGN PATENT DOCUMENTS

CN 101461711 A 6/2009
EP 2269691 A2 1/2011
(Continued)

OTHER PUBLICATIONS

Houben, R.P.M., et al, "Automatic mapping of human atrial fibrillation by template matching", Heart Rhythm, vol. 3, No. 10, Oct. 1, 2006, pp. 1221-1228.
(Continued)

*Primary Examiner* — Carl H Layno
*Assistant Examiner* — Jennifer L Ghand
(74) *Attorney, Agent, or Firm* — Scott Davison; Eleanor Musick; Musick Davison LLP

(57) ABSTRACT

An example system and method associated with identifying and treating a source of a heart rhythm disorder are disclosed. In accordance with therewith, a spatial element associated with a region of the heart is selected. Progressive rotational activations or progressive focal activations are determined in relation to the selected spatial element. A plurality of indexes of progressive rotational activations or progressive focal activations over time is formed. One or more indexes are selected from the plurality of indexes that
(Continued)

indicate consistency of the successive rotational activations or the progressive focal activations in relation to a portion of the region of the heart.

45 Claims, 26 Drawing Sheets

Related U.S. Application Data

(60) Provisional application No. 61/973,626, filed on Apr. 1, 2014.

(51) Int. Cl.
  *A61N 1/32* (2006.01)
  *A61N 1/368* (2006.01)
  *A61B 5/00* (2006.01)
  *A61B 5/042* (2006.01)
  *A61B 18/00* (2006.01)

(52) U.S. Cl.
  CPC .............. *A61B 18/12* (2013.01); *A61N 1/327* (2013.01); *A61N 1/368* (2013.01); *A61B 2018/00577* (2013.01)

(56) References Cited

U.S. PATENT DOCUMENTS

| | | |
|---|---|---|
| 4,754,763 A | 7/1988 | Doemland |
| 4,905,707 A | 3/1990 | Davies et al. |
| 4,905,708 A | 3/1990 | Davies |
| 5,029,082 A | 7/1991 | Shen et al. |
| 5,092,341 A | 3/1992 | Kelen |
| 5,121,750 A | 6/1992 | Katims |
| 5,172,699 A | 12/1992 | Svenson et al. |
| 5,178,154 A | 1/1993 | Ackmann et al. |
| 5,366,487 A | 11/1994 | Adams et al. |
| 5,427,112 A | 6/1995 | Noren et al. |
| 5,433,198 A | 7/1995 | Desai |
| 5,439,483 A | 8/1995 | Duong-Van |
| 5,450,846 A | 9/1995 | Goldreyer |
| 5,458,621 A | 10/1995 | White et al. |
| 5,480,422 A | 1/1996 | Ben-Haim |
| 5,487,391 A | 1/1996 | Panescu |
| 5,582,173 A | 12/1996 | Li |
| 5,645,070 A | 7/1997 | Turcott |
| 5,657,755 A | 8/1997 | Desai |
| 5,662,108 A | 9/1997 | Budd et al. |
| 5,687,737 A | 11/1997 | Branham et al. |
| 5,718,241 A | 2/1998 | Ben-Haim et al. |
| 5,795,303 A | 8/1998 | Swanson et al. |
| 5,810,740 A | 9/1998 | Paisner |
| 5,817,134 A | 10/1998 | Greenhut et al. |
| 5,819,740 A | 10/1998 | Muhlenberg |
| 5,836,889 A | 11/1998 | Wyborny et al. |
| 5,840,025 A | 11/1998 | Ben-Haim |
| 5,848,972 A | 12/1998 | Triedman et al. |
| 5,868,680 A | 2/1999 | Steiner et al. |
| 5,954,661 A | 9/1999 | Greenspon et al. |
| 5,954,665 A | 9/1999 | Ben-Haim |
| 6,052,618 A | 4/2000 | Dahlke et al. |
| 6,066,094 A | 5/2000 | Ben-Haim |
| 6,115,628 A | 5/2000 | Stadler et al. |
| 6,097,983 A | 8/2000 | Strandberg |
| 6,112,117 A | 8/2000 | Kenknight et al. |
| 6,188,924 B1 | 2/2001 | Swanson et al. |
| 6,208,888 B1 | 3/2001 | Yonce |
| 6,236,883 B1 | 5/2001 | Ciaccio et al. |
| 6,251,125 B1 | 6/2001 | Kenknight et al. |
| 6,256,540 B1 | 7/2001 | Panescu et al. |
| 6,301,496 B1 | 10/2001 | Reisfeld |
| 6,324,421 B1 | 11/2001 | Stadler et al. |
| 6,360,121 B1 | 3/2002 | Shoda |
| 6,397,100 B2 | 5/2002 | Stadler et al. |
| 6,438,406 B2 | 8/2002 | Yonce |
| 6,438,409 B1 | 8/2002 | Malik et al. |
| 6,449,503 B1 | 9/2002 | Hsu |
| 6,510,339 B2 | 1/2003 | Kovtun et al. |
| 6,522,905 B2 | 2/2003 | Desai |
| 6,539,256 B1 | 3/2003 | Kenknight et al. |
| 6,542,773 B2 | 4/2003 | Dupree et al. |
| 6,553,251 B1 | 4/2003 | Lähdesmäki |
| 6,584,345 B2 | 6/2003 | Govari |
| 6,725,085 B2 | 4/2004 | Schwartzman et al. |
| 6,738,655 B1 | 5/2004 | Sen et al. |
| 6,788,969 B2 | 9/2004 | Dupree et al. |
| 6,847,839 B2 | 1/2005 | Ciaccio et al. |
| 6,856,830 B2 | 2/2005 | He |
| 6,889,081 B2 | 5/2005 | Hsu |
| 6,892,091 B1 | 5/2005 | Ben-Haim et al. |
| 6,920,350 B2 | 7/2005 | Xue et al. |
| 6,941,166 B2 | 9/2005 | MacAdam et al. |
| 6,950,696 B2 | 9/2005 | Bjorling et al. |
| 6,950,702 B2 | 9/2005 | Sweeney |
| 6,959,212 B2 | 10/2005 | Hsu et al. |
| 6,975,900 B2 | 12/2005 | Rudy et al. |
| 6,978,168 B2 | 12/2005 | Beatty et al. |
| 6,985,768 B2 | 1/2006 | Hemming et al. |
| 7,016,719 B2 | 3/2006 | Rudy et al. |
| 7,043,292 B2 | 5/2006 | Tarjan et al. |
| 7,076,288 B2 | 7/2006 | Skinner |
| 7,117,030 B2 | 10/2006 | Berenfeld |
| 7,123,954 B2 | 10/2006 | Narayan et al. |
| 7,206,630 B1 | 4/2007 | Tarler |
| 7,215,993 B2 | 5/2007 | Lin |
| 7,245,962 B2 | 7/2007 | Ciaccio et al. |
| 7,263,397 B2 | 8/2007 | Hauck et al. |
| 7,283,865 B2 | 10/2007 | Noren |
| 7,289,843 B2 | 10/2007 | Beatty et al. |
| 7,289,845 B2 | 10/2007 | Sweeney et al. |
| 7,328,063 B2 | 2/2008 | Zhang et al. |
| 7,369,890 B2 | 5/2008 | Lovett |
| 7,457,664 B2 | 11/2008 | Zhang et al. |
| 7,505,810 B2 | 3/2009 | Harlev et al. |
| 7,509,170 B2 | 3/2009 | Zhang et al. |
| 7,515,954 B2 | 4/2009 | Harlev et al. |
| 7,567,835 B2 | 7/2009 | Gunderson et al. |
| 7,580,744 B2 | 8/2009 | Hsu |
| 7,620,446 B2 | 11/2009 | Ferek-Petric |
| 7,657,307 B2 | 2/2010 | Dam et al. |
| 7,729,753 B2 | 6/2010 | Kremliovsky et al. |
| 7,734,333 B2 | 6/2010 | Ghanem et al. |
| 7,734,336 B2 | 6/2010 | Ghanem et al. |
| 7,738,948 B2 | 6/2010 | Rouw et al. |
| 7,742,812 B2 | 6/2010 | Ghanem et al. |
| 7,751,882 B1 | 7/2010 | Helland |
| 7,761,142 B2 | 7/2010 | Ghanem et al. |
| 7,761,150 B2 | 7/2010 | Ghanem et al. |
| 7,769,452 B2 | 8/2010 | Ghanem et al. |
| 7,801,594 B1 | 9/2010 | Higham |
| 7,907,993 B2 | 3/2011 | Ghanem et al. |
| 7,907,994 B2 | 3/2011 | Stolarski et al. |
| 7,930,018 B2 | 4/2011 | Harlev et al. |
| 7,930,020 B2 | 4/2011 | Zhang et al. |
| 7,953,475 B2 | 5/2011 | Harlev et al. |
| 7,962,202 B2 | 6/2011 | Bhunia |
| 8,050,732 B2 | 11/2011 | Desai |
| 8,050,751 B2 | 11/2011 | Zhang et al. |
| 8,050,757 B2 | 11/2011 | Hsu |
| 8,095,205 B2 | 1/2012 | Bhunia |
| 8,095,206 B2 | 1/2012 | Ghanem et al. |
| 8,160,684 B2 | 4/2012 | Ghanem et al. |
| 8,165,666 B1 | 4/2012 | Briggs et al. |
| 8,165,671 B2 | 4/2012 | Freeman et al. |
| 8,175,702 B2 | 5/2012 | Efimov et al. |
| 8,306,618 B2 | 11/2012 | Ghanem et al. |
| 8,315,697 B2 | 11/2012 | Hsu |
| 8,340,766 B2 | 12/2012 | Ryu et al. |
| 8,386,024 B2 | 2/2013 | Gunderson et al. |
| 8,435,185 B2 | 5/2013 | Ghanem et al. |
| 8,489,171 B2 | 7/2013 | Hauck et al. |
| 8,521,266 B2 | 8/2013 | Narayan et al. |
| 8,588,885 B2 | 11/2013 | Hall et al. |
| 8,594,777 B2 | 11/2013 | Briggs et al. |

(56) References Cited

U.S. PATENT DOCUMENTS

| | | |
|---|---|---|
| 8,639,325 B2 | 1/2014 | Efimov et al. |
| 8,676,303 B2 | 3/2014 | Narayan |
| 8,700,140 B2 | 4/2014 | Narayan et al. |
| 8,715,199 B1 | 5/2014 | Macneil et al. |
| 8,812,074 B2 | 8/2014 | Kordis et al. |
| 8,838,222 B2 | 9/2014 | Narayan et al. |
| 8,838,223 B2 | 9/2014 | Narayan et al. |
| 8,868,169 B2 | 10/2014 | Narayan et al. |
| 9,031,642 B2 | 5/2015 | Ghosh |
| 9,050,006 B2 | 6/2015 | Narayan et al. |
| 9,055,876 B2 | 6/2015 | Narayan et al. |
| 9,055,877 B2 | 6/2015 | Narayan et al. |
| 9,055,878 B2 | 6/2015 | Narayan et al. |
| 9,089,269 B2 | 7/2015 | Narayan et al. |
| 9,107,600 B2 | 8/2015 | Narayan et al. |
| 9,220,427 B2 | 12/2015 | Narayan et al. |
| 9,241,667 B2 | 1/2016 | Narayan et al. |
| 9,282,910 B2 | 3/2016 | Narayan et al. |
| 9,332,915 B2 | 5/2016 | Narayan et al. |
| 9,375,156 B2 | 6/2016 | Narayan et al. |
| 9,380,950 B2 | 7/2016 | Narayan et al. |
| 9,392,948 B2 | 7/2016 | Briggs et al. |
| 9,393,425 B2 | 7/2016 | Narayan |
| 9,398,860 B2 | 7/2016 | Macneil et al. |
| 9,398,883 B2 | 7/2016 | Narayan et al. |
| 9,408,536 B2 | 8/2016 | Narayan et al. |
| 9,439,573 B2 | 9/2016 | Narayan et al. |
| 9,468,387 B2 | 10/2016 | Narayan et al. |
| 9,668,666 B2 | 6/2017 | Narayan et al. |
| 9,955,879 B2 | 5/2018 | Narayan et al. |
| 2002/0010392 A1 | 1/2002 | Desai |
| 2003/0018277 A1 | 1/2003 | He |
| 2003/0083587 A1 | 5/2003 | Ferek-Petric |
| 2003/0236466 A1 | 12/2003 | Tarjan |
| 2004/0073262 A1 | 4/2004 | Lovett |
| 2004/0093035 A1 | 5/2004 | Schwartz et al. |
| 2004/0243014 A1 | 12/2004 | Lee et al. |
| 2005/0137638 A1 | 6/2005 | Yonce et al. |
| 2005/0148892 A1 | 7/2005 | Desai |
| 2005/0203502 A1 | 9/2005 | Boveja et al. |
| 2006/0084970 A1 | 4/2006 | Beatty et al. |
| 2006/0161069 A1 | 7/2006 | Li |
| 2006/0161206 A1 | 7/2006 | Efimov et al. |
| 2007/0016261 A1 | 1/2007 | Dong et al. |
| 2007/0055167 A1 | 9/2007 | Bullinga |
| 2007/0208260 A1 | 9/2007 | Afonso |
| 2007/0208263 A1 | 9/2007 | John et al. |
| 2007/0232948 A1 | 10/2007 | Stadler et al. |
| 2007/0299351 A1 | 12/2007 | Harlev et al. |
| 2008/0097539 A1 | 4/2008 | Belalcazar |
| 2008/0109041 A1 | 5/2008 | De Voir |
| 2008/0114258 A1 | 5/2008 | Zhang et al. |
| 2008/0208012 A1 | 8/2008 | Ali |
| 2008/0319332 A1 | 12/2008 | Sommo et al. |
| 2009/0069704 A1 | 3/2009 | MacAdam et al. |
| 2009/0099468 A1 | 4/2009 | Thiagalingam et al. |
| 2009/0099618 A1 | 4/2009 | Rousso et al. |
| 2009/0112106 A1 | 4/2009 | Zhang et al. |
| 2009/0112110 A1 | 4/2009 | Zhang et al. |
| 2009/0112199 A1 | 4/2009 | Zhang et al. |
| 2009/0131760 A1 | 5/2009 | Ali et al. |
| 2009/0163968 A1 | 6/2009 | Donofrio |
| 2009/0177071 A1 | 7/2009 | Harlev et al. |
| 2009/0177072 A1 | 7/2009 | Harlev et al. |
| 2009/0259266 A1 | 10/2009 | Zhang et al. |
| 2009/0299203 A1 | 12/2009 | de Voir et al. |
| 2009/0299424 A1 | 12/2009 | Narayan |
| 2010/0026543 A1 | 2/2010 | Tsai et al. |
| 2010/0094274 A1 | 4/2010 | Narayan |
| 2010/0204592 A1 | 8/2010 | Hatib et al. |
| 2010/0217143 A1 | 8/2010 | Whittington et al. |
| 2010/0249627 A1 | 9/2010 | Zhang |
| 2010/0298729 A1 | 11/2010 | Zhang et al. |
| 2010/0305456 A1 | 12/2010 | Brainard, II |
| 2010/0324435 A1 | 12/2010 | Higham |
| 2011/0077540 A1 | 3/2011 | Belalcazar |
| 2011/0087121 A1 | 4/2011 | Zhang et al. |
| 2011/0112425 A1 | 5/2011 | Muhlsteff et al. |
| 2011/0118803 A1 | 5/2011 | Hou et al. |
| 2011/0130801 A1 | 6/2011 | Maskara et al. |
| 2011/0196249 A1 | 8/2011 | Staeuber et al. |
| 2011/0251505 A1 | 10/2011 | Narayan |
| 2011/0257547 A1 | 10/2011 | Zhang et al. |
| 2011/0282227 A1 | 11/2011 | Zhang et al. |
| 2012/0184858 A1 | 7/2012 | Harley et al. |
| 2012/0184863 A1 | 7/2012 | Harley et al. |
| 2012/0232417 A1 | 9/2012 | Zhang et al. |
| 2013/0006131 A1 | 1/2013 | Narayan et al. |
| 2013/0150740 A1 | 6/2013 | Narayan et al. |
| 2013/0150742 A1 | 6/2013 | Briggs et al. |
| 2013/0226016 A1 | 8/2013 | Narayan et al. |
| 2013/0245474 A1 | 9/2013 | Nicolson et al. |
| 2013/0324871 A1 | 12/2013 | Dubois et al. |
| 2013/0331718 A1 | 12/2013 | Narayan et al. |
| 2013/0345577 A1 | 12/2013 | Thakur et al. |
| 2014/0005562 A1 | 1/2014 | Bunch et al. |
| 2014/0066787 A1 | 3/2014 | Narayan et al. |
| 2014/0073981 A1 | 3/2014 | Narayan et al. |
| 2014/0114204 A1 | 4/2014 | Narayan et al. |
| 2014/0200467 A1 | 7/2014 | Strom et al. |
| 2014/0228696 A1 | 8/2014 | Narayan et al. |
| 2014/0336520 A1* | 11/2014 | Zeng .................... A61B 5/0452 600/516 |
| 2014/0371609 A1 | 12/2014 | Narayan et al. |
| 2014/0371613 A1 | 12/2014 | Narayan et al. |
| 2015/0038861 A1 | 2/2015 | Narayan et al. |
| 2015/0366476 A1 | 12/2015 | Laughner et al. |
| 2016/0015283 A1 | 1/2016 | Narayan et al. |
| 2016/0022163 A1 | 1/2016 | Narayan et al. |
| 2016/0166167 A1 | 6/2016 | Narayan et al. |
| 2016/0262643 A1 | 9/2016 | Ng et al. |
| 2016/0278657 A1 | 9/2016 | Narayan et al. |
| 2016/0302734 A1 | 10/2016 | Narayan |
| 2017/0049402 A1 | 2/2017 | Narayan et al. |
| 2017/0232263 A1 | 8/2017 | Narayan |
| 2017/0245774 A1 | 8/2017 | Narayan et al. |
| 2017/0311835 A1 | 11/2017 | Narayan et al. |
| 2017/0340229 A1 | 11/2017 | Narayan et al. |

FOREIGN PATENT DOCUMENTS

| | | |
|---|---|---|
| EP | 1808124 B1 | 4/2011 |
| EP | 2638854 A1 | 9/2013 |
| JP | H05502816 A | 5/1993 |
| JP | H09215667 A | 8/1997 |
| WO | 1991019452 A1 | 12/1991 |
| WO | 1994021168 A1 | 9/1994 |
| WO | 1996025096 A1 | 8/1996 |
| WO | 2005035046 A2 | 4/2005 |
| WO | 2005115232 A1 | 12/2005 |
| WO | 2006060366 A2 | 6/2006 |
| WO | 2007078421 A2 | 7/2007 |
| WO | 2007106829 A2 | 9/2007 |
| WO | 2008035070 A3 | 3/2008 |
| WO | 2013150740 A1 | 10/2013 |

OTHER PUBLICATIONS

Nademanee, Koonlawee, et al., "A new approach for catheter ablation of atrial fibrillation: mapping of the electrophysiologic substrate", J. Amer.Coll.Cardiol., vol. 43, No. 11, Jun. 2, 2004, pp. 2044-2053.

Narayan, S.M., et al., "Dynamics factors preceding the initiation of atrial fibrillation in humans", Heart Rhythm, vol. 5, No. 6, Jun. 1, 2008, pp. S22-S25.

Ciaccio, Edward J. et al., "Development of Gradient Descent Adaptive Algorithms to Remove Common Mode Artifact for Improvement of Cardiovascular Signal Quality", Annals of Biomedical Engineering, vol. 35, No. 7, Jul. 2007, pp. 1146-1155.

Sornborger, Andrew, et al., "Extraction of Periodic Multivariate Signals: Mapping of Voltage-Dependent Dye Fluorescence in the

(56) References Cited

OTHER PUBLICATIONS

Mouse Heart", IEEE Transactions on Medical Imaging, vol. 22, No. 12, Dec. 2003, pp. 1537-1549.
Sun, Yan, et al., "Characteristic wave detection in ECG signal using morphological transform", BMC Cardiovascular Disorders, vol. 5, No. 28, 2005.
Tai, Dean C.S., et al., "Correction of motion artifact in transmembrane voltage-sensitive fluorescent dye emission in hearts", Am. J. Physiol. Heart Circ. Physiol., vol. 287, 2004, pp. H985-H993.
Lin, Y-J, et al., "Electrophyiological Characteristics and Catheter Ablation in Patients With Paroxysmal Right Atrial Fibrillation", Circulation, Sep. 20, 2005; 112(12): 1692-1700, EPub Sep. 12, 2005.
Houben, R.P.M., et al., "Processing of Intracardiac Electrograms in Atrial Fibrillation", IEEE Engineering in Medicine and Biology Magazine, 2006, Nov./Dec., pp. 40-51.
Saksena, S., et al., "Regional Endocardial Mapping of Spontaneous and Induced Atrial Fibrillation in Patients With Heart Disease and Refractory Atrial Fibrillation", Am J Cardiol, 1999; 84:880-889.
EP 12711553 Supplementary European Search Report & European Search Opinion , dated Sep. 11, 2013, 7 pages.
PCT/US2012/029935 International Search Report and Written Opinion, dated Nov. 8, 2012, 9 pages.
EP 09819953 Supplementary European Search Report & European Search Opinion dated Feb. 7, 2012, 12 pages.
PCT/US2011/031468 International Preliminary Report on Patentability and Written Opinion, dated Oct. 9, 2012, 8 pages.
PCT/US2011/031470 International Preliminary Report on Patentability and Written Opinion, dated Oct. 9, 2012, 7 pages.
PCT/US2009/060178 International Preliminary Report on Patentability and Written Opinion, dated Apr. 12, 2011, 10 pages.
PCT/US2012/036157 International Preliminary Report on Patentability and Written Opinion , dated Aug. 14, 2012, 8 pages.
PCT/US2012/068639 International Preliminary Report on Patentability and Written Opinion, dated Jun. 10, 2013; 6 pages.
PCT/US/2014/029645 International Search Report and Written Opinion, dated Aug. 18, 2014, 17 pages.
PCT/US2012/068640 International Preliminary Report on Patentability and Written Opinion, dated Jun. 10, 2013; 5 pages.
PCT/US2014/029616 International Search Report and Written Opinion, dated Sep. 18, 2014; 9 pages.
Umapathy, K, et al. "Spatiotemporal Frequency Analysis of Ventricular Fibrillation in Explanted Human Hearts," IEEE Transactions in Biomedical Engineering, IEEE Service Center, Piscataway, NJ USA, vol. 56, No. 2, Feb. 1, 2009, pp. 328-335.
Kalifa, J, et al. "Mechanisms of wave fractionation at boundaries of high-frequency excitation in the posterior left atrium of the isolated sheep heart during atrial fibrillation," Circulation, vol. 113, No. 5, Feb. 7, 2006, pp. 626-633.
Yenn-Jiang L, et al. "Electrophysiological Mechanisms and Catheter Ablation of Complex Atrial Arrhythmias from Crista Terminalis: Insight from Three-Dimentional Noncontact Mapping," Pacing and Clinical Electrophysiology, vol. 27, No. 9, Sep. 1, 2004, pp. 1231-1239.

Supplementary European Search Report & European Search Opinion issued in EP 12779506.0, dated Nov. 18, 2014, 8 pages.
Eckman, et al. "Recurrence plots of dynamical systems," Europhys. Lett., 4 (3), Nov. 1, 1987 pp. 973-977.
EP12855266.8: Supplementary European Search Report & European Search Opinion, dated Jun. 2, 2015, 9 pages.
EP12855738.6: Supplementary European Search Report & European Search Opinion, dated Jun. 5, 2015, 9 pages.
EP14763969.4 Supplementary European Search Report & European Search Opinion dated Oct. 21, 2016, 7 pages.
EP15192804.1 Supplementary European Search Report, dated Feb. 18, 2016, 7 pages.
Holm, M. et al., "A New Method for Analysis of Atrial Activation During Chronic Atrial Fibrillation in Man", IEEE Transactions on Biomedical Engineering, vol. 43, No. 2, Feb. 1, 1996, pp. 198-210.
Jung, TP et al, Removing Electroencephalographic Artifacts by Blind Source Separation, Psychophysiology, 37.02 (2000): 163-178.
Kadish, A., et al., "Characterization of fibrillatory rhythms by ensemble vector directional analysis", Am J Physiol.—Heart Circ. Physiol., vol. 285, Oct. 2003, pp. H1705-H1719.
Masse, S., et al., "Wave similarity of human ventricular fibrillation from bipolar electrograms", Eurospace (2007) vol. 9, pp. 10-19.
PCT/US2015/023929, International Search Report and Written Opinion, dated Jul. 9, 2015, 8 pages.
PCT/US2015/046742 International Search Report and Written Opinion; dated Dec. 1, 2015, 5 pages.
Ulphani, J.S., et al., "Frequency gradients during two different forms of fibrillation in canine atria", Heart Rhythm, vol. 4, No. 10, Oct. 2007, pp. 1315-1323.
Umapathy, K, et al. "Spatiotemporal Frequency Analysis of Ventricular Fibrillation in Explanted Human Hearts," IEEE Transactions in Biomedical Engineering, IEEE Service Center, Piscataway, NJ USA, vol. 56, No. 2, Feb. 1, 2009, pp. 238-335.
Botteron, G.W. et al., A technique for measurement of the extent of spatial organization of atrial activation during atrial fibrillation in the intact human heart, IEEE Transactions on Biomedical Engineering, Jun. 1995, pp. 579-586, vol. 42, No. 6.
Censi, F. et al., "Recurrent Patterns of Atrial Depolarization During Atrial Fibrillation Assessed by Recurrence Plot Quantification", Annals of Biomedical Engineering, 2000, pp. 61-70; vol. 28.
EP15774130.7 Supplementary European Search Report & European Search Opinion, dated Nov. 15, 2017, 9 pages.
EP15836641 Supplementary European Search Report & European Search Opinion, dated Mar. 8, 2018, 8 pages.
PCT/US2017/030683, International Search Report and Written Opinion, dated Aug. 1, 2017, 6 pages.
Xiao, Yuping et al., Parameter estimation of spiral waves from atrial electrograms:, Proceedings of International Conference on Acoustics, Speech and Signal Processing (ICASSP '03) Apr. 6-10, 2003, Hong Kong, China, IEEE, 2003 IEEE International Conference, vol. 5, Apr. 6, 2003, pp. V_245-V_248.

* cited by examiner

"Traditional" Mapping of Discontinuous Source

Clockwise Phase Singularity Continuous, While
Fibrillatory waves Interrupt Surrounding Spiral Arm Invasion of Source by Surrounding Activation.
(B) Perturbation of Spatial Locus
1. Stabilization of Locus
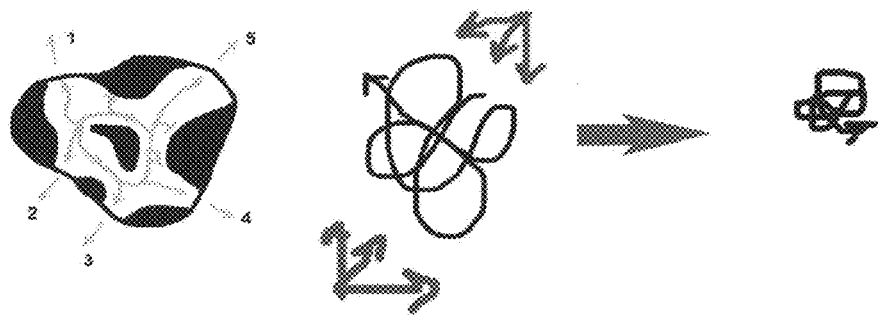
2. Destabilization of Locus
FIG. 19
Invasion of Source by Surrounding Activation. Termination.
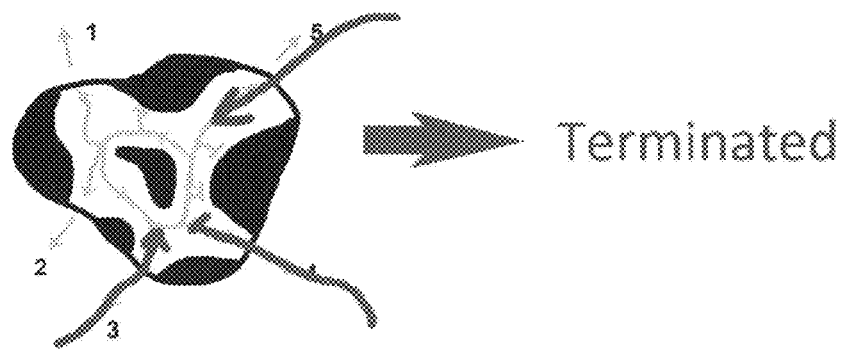
FIG. 20

SYSTEM AND METHOD OF IDENTIFYING SOURCES ASSOCIATED WITH BIOLOGICAL RHYTHM DISORDERS

RELATED APPLICATIONS

This application is a continuation-in-part of U.S. application Ser. No. 13/844,562, filed Mar. 15, 2013, now issued as U.S. Pat. No. 9,332,915, and claims the benefit of the priority of U.S. Provisional Application No. 61/973,626, filed Apr. 1, 2014, each of which is incorporated herein by reference in its entirety. This application further incorporates herein by reference in their entireties U.S. application Ser. No. 12/576,809, filed Oct. 9, 2009, issued as U.S. Pat. No. 8,521,266; U.S. application Ser. No. 13/081,411, filed Apr. 6, 2011, issued as U.S. Pat. No. 8,700,140; U.S. application Ser. No. 13/470,705, filed May 14, 2012; and U.S. application Ser. No. 13/559,868, filed Jul. 27, 2012.

GOVERNMENT RIGHTS

This invention was made with government support under Grants R01 HL83359 and HL103800 from the National Institutes of Health. The government has certain rights in the invention.

BACKGROUND

Field

The present application relates generally to biological rhythm disorders. More specifically, the present application is directed to a system and method of identifying a source (or sources) of a biological rhythm disorder, such as a heart rhythm disorder, by analyzing whether there exists continuous or interrupted activation associated with a source of a heart rhythm disorder (e.g., using a metric of progressive rotational or focal activation in relation to one or more spatial elements associated with the source of the heart rhythm disorder).

Brief Discussion of Related Art

Heart rhythm disorders are common and represent significant causes of morbidity and death throughout the world. Malfunction of the electrical system in the heart represents a proximate cause of heart rhythm disorders. Heart rhythm disorders exist in many forms, of which the most complex and difficult to treat are atrial fibrillation (AF), atrial tachycardias that interconvert and hence appear to fluctuate (IAT), multifocal atrial tachycardia (MAT), polymorphic ventricular tachycardia (VT) and ventricular fibrillation (VF). Other rhythm disorders are more simple and often easier to treat, but may also be clinically significant including atrial tachycardia (AT), supraventricular tachycardia (SVT), atrial flutter (AFL), premature atrial complexes/beats (SVE) and premature ventricular complexes/beats (PVC). While under normal conditions the sinus node keeps the heart in sinus rhythm, under certain conditions rapid activation of the normal sinus node can cause inappropriate sinus tachycardia or sinus node reentry, both of which also represent heart rhythm disorders.

Treatment of heart rhythm disorders—particularly complex rhythm disorders of AF, VF and VT—can be very difficult. Pharmacologic therapy for complex rhythm disorder is not optimal. Ablation has been used increasingly in connection with heart rhythm disorders by maneuvering a sensor/probe to the heart through the blood vessels, or directly at surgery, and delivering energy to a location of the heart to mitigate and in some cases to eliminate the heart rhythm disorder. However, in complex rhythm disorders ablation is often difficult and ineffectual because tools that identify and locate a cause (source) of the heart rhythm disorder are poor and hinder attempts to deliver energy to a correct region of the heart to eliminate the disorder.

Certain systems and methods are known for treating simple heart rhythm disorders. In a simple heart rhythm disorder (e.g., atrial tachycardia), the source of the disorder can be identified by tracing activation back to the earliest location, which can be ablated to mitigate and in some cases to eliminate the disorder. However, even in simple heart rhythm disorders, ablating the cause of a heart rhythm disorder is challenging and experienced practitioners often require hours to ablate simple rhythm disorders that show consistent beat-to-beat activation patterns, such as atrial tachycardia.

There are few, if any, known systems and methods that have been successful with respect to identifying the sources or causes for the direct treatment of complex rhythm disorders such as AF, VF or polymorphic VT. In a complex rhythm disorder, an earliest location of activation onsets cannot be identified because activation onset patterns change from beat to beat and are often continuous without an earliest or a latest point.

Diagnosing and treating heart rhythm disorders generally involves the introduction of a catheter having a plurality of sensors/probes into the heart through blood vessels of a patient. The sensors detect electric activity of the heart at sensor locations in the heart. The electric activity is generally processed into electrogram signals that represent the activation of the heart at the sensor locations.

In a simple heart rhythm disorder, the signal at each sensor location is generally consistent from beat to beat, enabling identification of the earliest activation. However, in a complex rhythm disorder, the signal at each sensor location from beat to beat may transition between one, several, and multiple deflections of various shapes. For instance, when a signal for a sensor location in AF includes 5, 7, 11 or more deflections, it is difficult if not impossible to identify which deflections in the signal are local to the sensor location in the heart (i.e., local activation onset) versus a nearby sensor location in the heart (i.e., far-field activation onset) or simply noise from another part of the patient's heart, other anatomic structures or external electronic systems. The foregoing deflections make it difficult if not impossible to identify activation onset times of the beats in a signal at a sensor location.

Strategies in complex rhythm disorders have also considered regularity in signals at sensor locations as a surrogate for the source of the complex rhythm disorder, i.e., the source being more organized at certain sensor locations than at adjacent sensor locations. For example, U.S. Pat. No. 7,117,030 by Berenfeld et al. and U.S. Pat. No. 5,792,189 by Gray et al. exemplify approaches in which the source(s) for variable atrial fibrillation (AF) are considered highly regular and rapid. However, while these approaches have been validated in animal models, they may not be successful in finding and treating sources of atrial fibrillation in humans. As an example, Sanders et al. (Circulation 2005) found that locations of regularity, indicated by high spectral dominant frequency with a high regularity index, were rarely the locations where AF terminated by ablation in complex (persistent) AF. Other studies such as Sahadevan (Circulation 2004) identified locations of rapid regular activity in human AF that have not been shown to drive human AF. Animal models (Kalifa, Circulation 2006) and human studies (Nademanee, J Am Coll 2004) suggest that complex fractionated atrial electrograms (CFAE) may surround regular 'drivers' and may cause variable activation during AF. In clinical use, however, such CFAE sites reflect several competing and quite different phenomena, of which some are relevant to the causes of a heart rhythm disorder and others represent noise or artifact (Konings, Circulation 1997; Narayan, Heart Rhythm 2011; Calkins, Heart Rhythm 2012). As a result, CFAE are often unstable (e.g., varying in location over time or disappearing altogether), are found in large and widespread areas of heart tissue rather than being just in small discrete areas, and are usually identified inconsistently by a variety of relatively subjective criteria. Therefore, CFAE sites, in larger multicenter trials, have turned out to be poor targets for AF treatment with long term success (Oral, Circulation 2007; Oral J Am Coll Cardiol, 2009).

Accordingly, it is desirable to provide a system and method for detecting a source (or sources) of a heart rhythm disorder, particularly complex rhythm disorder including atrial fibrillation, interconverting or multifocal atrial tachycardias, polymorphic ventricular tachycardia or ventricular fibrillation, in the midst of complex colliding waves, competing sources and/or noise, which cause disorganization near the source, e.g., core of the disorder.

SUMMARY

The present application is applicable to identifying sources of various rhythms and directly using this information to treat the rhythm disorder. It is also applicable to normal and disordered heart rhythms, as well as other biological rhythms and rhythm disorders, such as neurological seizures, esophageal spasms, bladder instability, irritable bowel syndrome, and other biological disorders for which biological signals can be recorded to permit determination, diagnosis, and/or treatment of the cause (or source) of the disorders. This application does not rely on activation mapping or examining regions of the biological organ (e.g., heart) that exhibit similar voltages (isopotential mapping) at sensor locations. It is thus particularly useful in complex rhythm disorders that exhibit complex activation patterns and complex varying signals, and is able to identify the source(s) of the complex rhythm disorders even if the sources are influenced and appear to be modified by such complex signals. It is especially useful in identifying the cause(s) of the disorders of the heart rhythm such that they can be treated with expediency.

The source indicates a region of the organ (e.g., heart) from where activation emanates to cause the complex rhythm disorder. Sources may include rotational circuits (rotors), from where waves, typically spiral waves, emanate to cause disorganized activation. Sources may also include focal impulse regions (e.g., focal sources), from where activation emanates centrifugally to cause disorganized activation.

The present application addresses several problems that have prevented the identification of sources for human complex rhythm disorders using methods routinely and historically applied to simple rhythm disorders. Using traditional analyses, electrogram shapes are often difficult to interpret in complex rhythm disorders. Sources precess (move) in limited spatial areas, such that traditional analyses from a fixed set of electrodes may not comprehend rotational activation (associated with a rotor) or centrifugal activation (associated with a focal source) when the source moves relative to the electrodes during and between consecutive beats. Disorganized activation from within or without the tissue can perturb and interrupt the spiral arms emanating from the rotor, which obscures rotation using traditional analyses (e.g., FIGS. 15-17 and 21). Electrical noise due to a variety of reasons, such as movement artifact from the movement of recording sensors or their physiological interface (e.g. body surface, cardiac tissue, etc.), poor electrode contact with the physiological interface, underlying electrical noise from the ambient environment, or near-field and far field signals, can make determination of activation particularly difficult in a rhythm with already underlying complexity.

Precession of the source can obscure detection of a rotational circuit on fixed electrodes, since, for instance, the rotational activation around the core to the left (for instance at 06:00 clock face position during clockwise rotation) will be obscured if the core moves to the right, and similarly for other movements of the rotor core relative to fixed electrode over time (e.g., FIG. 15). The present invention detects such rotational activation. It also enables detection of rotational activation along a perimeter that is not clearly circular and may be ellipsoid or have another shape depending on the refractoriness and conduction properties of surrounding tissue. Such non-circular perimeters will also confuse traditional recording approaches but can be detected by the present invention. Finally, this invention is able to detect rotational activation even if the sequence is interrupted along sectors (portions) of its perimeter ('circumference'), by disorganized waves as described herein.

Disorganized activation can have numerous effects on the source. First, disorganized activation can arise if activation from the source undergoes disorganization away from its center or core (e.g., FIG. 16, left display). In this case, disorganized activation can surround the source but not perturb it, in which case, the central functionality of the source is largely unperturbed. If the source is associated with a complex rhythm disorder, such disorganization is often termed "fibrillatory conduction" from the rotor or focal source. The present invention provides the ability to quantify fibrillatory conduction and to define its functional effect, neither of which was previously characterized. Disorganization (or fibrillatory conduction) can be due to functional properties such as abnormalities in repolarization, abnormalities in conduction, abnormalities in tissue capacitance, or abnormalities in impulse generation. This disorganization can also be due to the electrical impact of structural factors, such as heterogeneous cellular types (including fibrosis, scar, gene therapy or stem cell therapy), geometrical curvature of the organ (e.g., heart), or mechanical motion including stretch, piezoelectric effects and other manifestations of mechano-electrical feedback. This disorganization can also be due to abnormalities in nervous system function or innervation, such as the autonomic nervous system, resulting in abnormal spatially varying electrical properties in the tissue of the organ (e.g., heart).

Second, disorganized activation that surrounds the source but does not perturb it can also propagate towards the source from a second different spatially distinct region (e.g., FIG. 16, right display) or other cause of disorganization. The second source may be a second rotor or focal source of a complex rhythm (e.g. fibrillation). The second source may also be a simple rhythm within the body, such as the sinus nodal impulse (the body's internal pacemaker), a simple atrial tachycardia (e.g., typical atrial flutter), one or more spontaneous premature impulses (such as premature atrial complexes or PACs), one or more pacing impulses (e.g., from multiple leads of a cardiac pacemaker or biventricular or biatrial pacing device), a biological pacemaker from gene or other regenerative therapy, or other sources. The second source may also be outside the body, including external beam radiation, external pacing, external ablation energy sources, other electromagnetic radiation, or other sources. Disorganized activation at the interface between sources appears similar to "collision" or "fusion" as described in the literature in connection with simple rhythms or pacing, although its formation and its implications to treat human rhythm disorders in this invention are unique and distinct from that literature.

Third, disorganized activation can modify the source by altering its rate and/or regularity, while the source continues to operate (e.g., FIG. 17). Disorganized electrical waves can collide and may even combine with electrical components of source activation (e.g., similar to "fusion" in the literature on simple rhythms or pacing). This may alter the rate or regularity of the source, causing the source to appear irregular or complex (e.g., FIG. 18). A practical application of this invention is to tailor therapy to intentionally alter regularity of the source, convert the source to a simple regular rhythm that is more easily treated (e.g., atrial tachycardia), or to destabilize the source via complex oscillations (Frame and Simson, Circulation, 1988) such that the source self-terminates.

Fourth, disorganized activation can modify the source by altering its spatial location, while the source continues to operate (e.g., FIG. 19). This may cause the source to precess (move) in more constrained spatial areas, or potentially to meander in less constrained spatial areas. A practical application of the invention is to tailor therapy to intentionally modify the precession (limited spatial motion) of the source so that the source becomes fixed in a spatial area. This will essentially convert the source of a complex rhythm disorder into a simple rhythm disorder, such as an atrial tachycardia, that is relatively easy to treat. Treatment may thus be delivered using ablation, pacing strategies, gene or cellular therapy, or other forms of therapy. Another application of the invention is to intentionally alter the spatial location of the source to a region where it can no longer sustain, including inert regions of the organ (e.g., heart), to the edge of the organ, or even outside the organ.

Fifth, disorganized activation can invade the source to transiently terminate the source (e.g., FIG. 20). This can enable transient organization of the overall rhythm, or the source can be re-engaged. Re-engagement can take many forms. Re-engagement of the source (e.g., rotor) of a complex rhythm disorder, for instance, can take place in the opposite direction to its original activation sequence (e.g., clockwise whereas the source was formerly counterclockwise, or vice versa). This altered directionality may be more or less stable than the original direction. A practical application of the invention provides a potential therapy for the patient, by shifting activation of the source of a complex rhythm disorder (e.g., heart rhythm disorder) to a less stable form that is more easily treated and that may self-terminate.

Sixth, disorganized activation can invade the source and terminate for a prolonged period of time (e.g., FIG. 20). This can enable organization of the overall heart rhythm disorder into either normal (sinus) rhythm or a simple heart rhythm disorder that can be easily treated (e.g., atrial fibrillation converting to atrial tachycardia; ventricular fibrillation converting to ventricular tachycardia). This can also enable change in the disorganized activation such that it may be sustained only transiently by disorganized activity without sources, or sustained by another source. This can be the basis for treating the source, whether it is for a simple rhythm disorder, such as a regular impulse generating region or circuit within an organized surrounding activation, or for a complex rhythm disorder, such as an organized impulse generating region or circuit within disorganized surrounding activation.

Seventh, there are certain effects on the heart by treating arrhythmias, including residual heart rhythm disorders or, if the arrhythmia is eliminated, the subsequent risk for arrhythmias. Treatment may comprise elimination of all sources, modulation or elimination of source(s) with a predominant impact on the overall rhythm (dominant sources), or modulation/elimination of non-dominant sources.

Treatment of all sources should eliminate the arrhythmia in the long-term, although transiently the arrhythmia may continue transiently via disorganized activity ('fibrillatory conduction'). This transient fibrillatory conduction may be disorganized when measured by several metrics, and last from seconds to days. In the latter case, treatment may appear to result in "no apparent change" during the treatment procedure yet yield long-term treatment success (freedom from the arrhythmia). Cases have been observed when the arrhythmia (e.g., atrial fibrillation) terminates days or even weeks after treatment directed to sources by this approach and is then absent on follow-up for years.

Treatment of dominant source(s) may cause paradoxical disorganization of the arrhythmia, because regions are no longer organized by these source(s), yet may also yield long-term treatment success if remaining non-dominant sources are less capable of sustaining the arrhythmia alone.

Finally, treatment of non-dominant sources may cause organization of the arrhythmia using conventional analytical metrics. In this case, the remaining (dominant) source(s) may cause continued disease unless eliminated. As an example, this may include organized atrial tachycardias after ablation of AF that result from non-elimination of dominant sources. These considerations are critical for devising patient- and mechanism-tailored treatment strategies, i.e., precision medicine in the field of heart rhythm disorders.

This invention describes a system and method of determining whether rotational activation or focal activation is present during a heart rhythm disorder (e.g., complex heart rhythm disorder) within the context of electrical disturbances or noise mentioned above, and using this information to treat the human heart rhythm disorder in patients. In one embodiment, there is determined an index of progressive angular deviation (PAD), which indicates whether activation is rotational on one or more beats even if interruptions disrupt portions of the activation within any beat. Angles are assigned to progressively activating sites. If these sites demonstrate progressive angular deviation even if interrupted for a portion of the circumference due to physiology such as 'fibrillatory conduction', rotational activity is assigned. The same approach can be used to identify a focal source, as zero sum rotation in all directions (i.e. centrifugal activation) from a region of tissue. These regions can be targeted for treatment such as ablation as described below.

In another embodiment, the invention uses the polar coordinate system, to measure the concept of progressive angular deviation around a pivot point (or rotor core). In this embodiment, a rotational activation trail will produce a perfectly spiral polar plot, while a centrifugal focal activation trail will produce a pattern representing simultaneous activation of electrodes on successively larger concentric circles around the focal origin. As before, deviations from these representations indicate disruptions due to disorganization from the complex or 'noisy' milieu (e.g., atrial fibrillation, ventricular fibrillation).

In yet another embodiment, this invention uses vectorial approaches to demonstrate rotational or centrifugal (focal)

activation in simple or complex rhythm disorders. A vector is constructed that indicates the direction of activation, between electrode sites in a pair, and the speed of conduction between them, based upon differences in activation time and the relative distance. This is repeated for successive electrode pairs, then during and between successive heart beats (e.g., over time). Vectors that trace a circle are 'simple' reentry. If conduction slows for a portion, that arc of the circumference is shortened, making the vector loop more elliptical. This site of arc shortening (due to slow conduction) may be a prime target for therapy, such as ablation, drug therapy, pacing and so on.

The vectors may also trace an ellipse or another non-circular shape when the rotor core precesses. Vectorial analyses can also be computed using derived indexes such as principal components of activation (from mathematical principal component analysis), or modifications based on identifying sites that can be activated within a time period consistent with known conduction velocities of normal and abnormal tissue.

In yet another embodiment, this invention uses counting schemes to indicate activation consistent with rotation or focal activation, to yield a 'rotational number' or 'focal number'. The simplest counting scheme for rotational activity includes incrementing a rotational counter when a site along a circular trajectory is activated. This can be modified for an elliptical perimeter, such as by 'combining' adjacent electrode sites so that the circular trajectory may be compressed in one axis. A rotational circuit is identified when the rotational counter exceeds a threshold in a specified time span in a defined spatial region.

Similarly, the simplest counting scheme for focal activity includes incrementing a centrifugal counter when activation affects a site along one or more radial trajectories. A focal source is identified when the focal counter exceeds a threshold in a specified time span in a defined spatial region.

Other schemes to detect rotational or focal sources include statistical methods such as Shannon entropy. Another embodiment includes only counting sites that activate with a similar electrogram (signal) shape along a trajectory (circular or centrifugal), for instance tracking the activation path or trail for 'signature' electrograms. Such signatures may be 'fractionated', monophasic or show specific frequency/spectral patterns. This may include sites with a narrow fundamental frequency, indicating a predominant rate in that region. The activation trail, indicative of the source for a heart rhythm disorder, may be a modified rotational (circular or elliptical) trial, or modified focal (radial or anisotropic radial) trail.

A series of trigonometric indexes can also be constructed to indicate rotational activation, such as by using the sine function which rises progressively from 0 to 1, then to −1 then to 0 in a plausible time-period for sites within a defined spatial region. Analogous logic applies to the construction of other trigonometric indexes that use the cosine or other trigonometric, inverse trigonometric, hyperbolic or inverse hyperbolic functions.

In still another embodiment, correlation analyses are used. In this embodiment, a spatial pattern of activations indicative of a heart rhythm disorder (an activation trail) can be correlated to the pattern on successive cycles to determine if the pattern repeats, even if the pattern is interrupted by invading wavefronts or other disorganization in a complex rhythm disorder. This invention can also be used to find centrifugal activation (a 'focal beat') despite interruptions.

One concept embodied in the invention is that driver regions for an arrhythmia may be maintained by additional primary sources. For instance, a rotor or focal source may activate dependently with secondary sources in a "mother-daughter" fashion. Mother-daughter rotors should be synchronized in some fashion, potentially with a time-delay (or phase shift), and thus may be detected by correlation or phase methods to identify primary driver regions from secondary regions.

In all embodiments, rotational activations or focal activations can be identified in the midst of complex surrounding disorganization. In cases of simple rotational circuits (e.g., FIG. 21, "simple" display), the rotational, angular, vectorial or other sequence of representation are uninterrupted. However, this sequence becomes progressively less clear with greater and greater surrounding disorganization, interruption or "fibrillatory conduction" (e.g., FIG. 21, "precession, "discontinuous", and "interrupted" displays). Similarly, focal sources are identified in the midst of a complex arrhythmia with surrounding disorganization.

In each case of interrupted/discontinuous sources, how rotational or centrifugal activation trails are interrupted, spatially and temporally, can yield important information. If the interruptions are temporally reproducible, for instance at a specific rate, they may represent interruption from a secondary source. Such a source may be asynchronous to the source being measured. The spatial direction from which the interruption is detected, for instance, consistently from a septal or right atrial location, may indicate the relative direction from which additional source(s) occur. Such information can be used computationally to help detect potential sources from those directions, which can be targeted for improved treatment.

In the various embodiments, analyses of rotational or centrifugal (focal) activation are performed within a defined spatial region that encompasses an area of precession (limited meander or 'wobble') of a rotor or focal source of a rhythm disorder. In simple rhythm disorders, this precession area is very small (effectively zero, but actually non-zero due to slight stochastic changes in functional property of tissue over time). In complex rhythm disorders such as atrial fibrillation, the precession area of a source is on average 2-3 cm$^2$ (<10 cm$^2$) of tissue surface.

The area of precession, within which the source of the rhythm disorder is analyzed, can be varied. In particular, detection can be tailored to the diagnostic or treatment strategy employed. For instance, if an ablation catheter has a lesion diameter of 7 mm, the precession area of analysis need not be smaller than that.

Detection of areas of precession can be tailored to each patient. This can be based upon factors such as proximity of the analysis zone to regions of structural abnormality (scar or fibrosis), or abnormal regions of function (repolarization or conduction). In more sophisticated analyses, the precession area can be increased in patients with enlarged atria from a disease state called remodeling. The area may also increase in patients whose arrhythmia continues despite extensive prior ablation.

Factors that influence the precession area can be incorporated into a database, and accessed in software using a lookup table. This database may include, but is not limited to, patient gender, age, number of years with the rhythm disturbance, source locations, type of disorder (such as paroxysmal or persistent AF) and so on.

This invention enables a determination of a source (or sources) of the heart rhythm disorder for treatment. An advantage of the present method and system is that they can be carried out rapidly while a sensing device—such as a catheter having sensors thereon—is used in or near the patient and is followed by treatment of cardiac tissue to ameliorate the disorder and in many cases to cure the disorder. Treatment may thus occur immediately, since the invention will provide the location(s) of the source of the heart rhythm disorder.

In accordance with an embodiment, a method of identifying and treating a biological rhythm disorder is disclosed. In accordance with the method, cardiac signals are processed to measure rotating cardiac activity in a region of tissue and cardiac activity that is not part of the measured rotating cardiac activity in the region of tissue. One or more regions of tissue are determined wherein rotating cardiac activity predominates over non-rotating cardiac activity to define a rotational source (e.g., rotor). Alternatively, one or more regions of tissue are determined wherein centrifugal cardiac activity predominates over non-centrifugal cardiac activity to define a focal source. Such regions may interact and interconvert. At least one portion of the tissue is identified proximate to the source to enable selective modification of the at least one portion in order to treat the heart rhythm disorder.

In accordance with another embodiment, a system to identify and treat a biological rhythm is disclosed. The system includes a processor and a memory storing instructions that, when executed by the processor, cause the processor to perform the following operations. The operations include processing cardiac signals via a computing device to measure rotating cardiac activity in a region of tissue. The operations further include measuring cardiac activity that is not part of the measured rotating or centrifugal cardiac activity in said region of tissue. The operations also include determining one or more regions of tissue wherein rotating cardiac activity predominates over non-rotating cardiac activity to define a source. Furthermore, the operations include identifying at least one portion of the tissue proximate to the source to enable selective modification of the at least one portion in order to treat the heart rhythm disorder.

In accordance with further embodiment, a storage medium storing instructions that, when executed by the processor, cause the processor to perform the following operations is disclosed. The operations include processing cardiac signals via a computing device to measure rotating cardiac activity in a region of tissue. The operations further include measuring cardiac activity that is not part of the measured rotating cardiac activity in said region of tissue. The operations also include determining one or more regions of tissue wherein rotating cardiac activity predominates over non-rotating cardiac activity to define a source and. Furthermore, the operations include identifying at least one portion of the tissue proximate to the source to enable selective modification of the at least one portion in order to treat the heart rhythm disorder.

In accordance with an embodiment, a method of determining consistency of activation (repeatability even in noisy signals) associated with a heart rhythm disorder is disclosed. In accordance with the method, a spatial element associated with a region of the heart is selected. Progressive rotational activations or progressive focal (centrifugal) activations are determined in relation to the selected spatial element. A plurality of indexes of the progressive rotational activations or the progressive focal activations is formed. One or more indexes are selected from the plurality of indexes that indicate consistency of the progressive rotational activations or the progressive focal (centrifugal) activations in relation to a portion of the region of the heart.

In accordance with another embodiment, a system to determine consistency of activation associated with a heart rhythm disorder is disclosed. The system includes a processor and a memory storing instructions that, when executed by the processor, cause the processor to perform the following operations. The operations include selecting a spatial element associated with a region of the heart. The operations also include determining progressive rotational activations or progressive focal activations in relation to the selected spatial element. The operations further include forming a plurality of indexes of the progressive rotational activations or the progressive focal activations. Furthermore, the operations include selecting one or more indexes from the plurality of indexes that indicate consistency of the progressive rotational activations or the progressive focal activations in relation to a portion of the region of the heart.

In accordance with further embodiment, a storage medium storing instructions that, when executed by the processor, cause the processor to perform operations for determining consistency of activation associated with a heart rhythm disorder is disclosed. The operations include selecting a spatial element associated with a region of the heart. The operations also include determining progressive rotational activations or progressive focal activations in relation to the selected spatial element. The operations further include forming a plurality of indexes of the progressive rotational activations or the progressive focal activations. Furthermore, the operations include selecting one or more indexes from the plurality of indexes that indicate consistency of the progressive rotational activations or the progressive focal activations in relation to a portion of the region of the heart.

These and other purposes, goals and advantages of the present application will become apparent from the following detailed description of example embodiments read in connection with the accompanying drawings.

BRIEF DESCRIPTION OF THE DRAWINGS

Some embodiments are illustrated by way of example and not limitation in the figures of the accompanying drawings in which:

FIG. 19 indicates disorganization that perturbs the spatial localization of a source. (1) disorganization constrains spatial precession, making the source locus smaller and the rhythm more regular. (2) disorganization exacerbates source precession, the rotor precesses to another region of the heart, where it may self-terminate or be easier to treat;

FIG. 20 indicates disorganization that perturbs the source to the point of terminating the source of the disorder;

DETAILED DESCRIPTION

A system and method for identifying one or more sources of biological rhythm disorder (e.g., heart rhythm disorders) are disclosed herein. In the following description, for the purposes of explanation, numerous specific details are set forth in order to provide a thorough understanding of example embodiments. It will be evident, however, to one skilled in the art, that an example embodiment may be practiced without all of the disclosed specific details.

Figure 1:
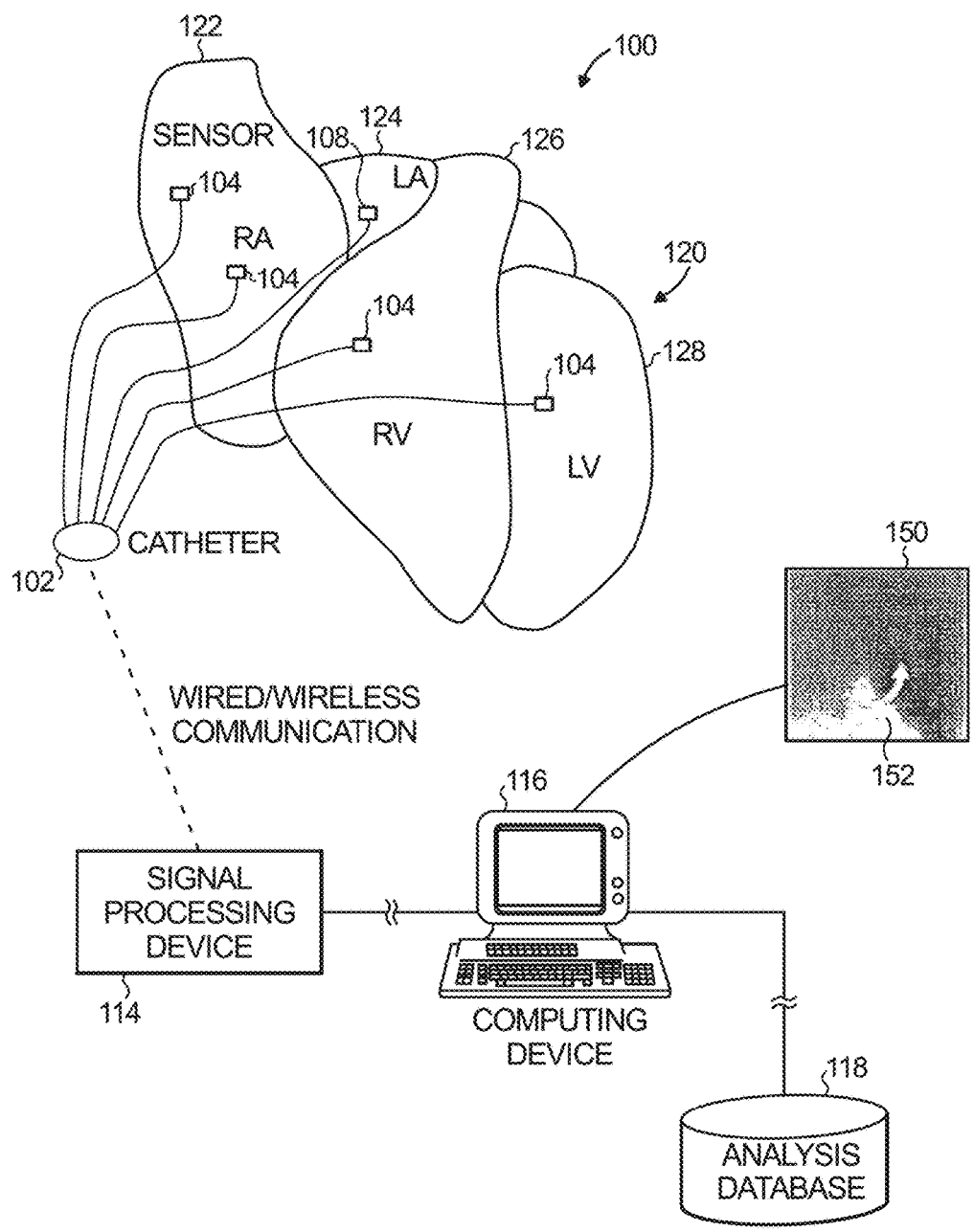
FIG. 1 illustrates an example system to identify a source (or sources) of a heart rhythm disorder.

FIG. 1 illustrates an example system 100 to identify a source (or sources) of a biological rhythm disorder (e.g., heart rhythm disorder) in a human patient. Specifically, the example system 100 is configured to access cardiac information (signals) collected/detected from the patient's heart in connection with the heart rhythm disorder. The system 100 is further configured to process the signals in order to determine at least one spatial area including one or more spatial elements about which there is progressive angular deviation (PAD) of activation (e.g., activation onset times) associated with other spatial elements for a number activation cycles. Progressive angular deviation will show rotation that proceeds around the spatial area even if the sequence is interrupted along sectors (portions) of its perimeter ('circumference'). This approach also enables detection of rotational activation in a perimeter that is not clearly circular and may be ellipsoid or have another shape depending on the refractoriness and conduction properties of surrounding tissue. A region of the heart associated with a spatial area can be selected for treatment (e.g., ablation) to ameliorate and in many cases to cure the heart rhythm disorder.

As shown in FIG. 1, the heart includes a right atrium 122, left atrium 124, right ventricle 126 and left ventricle 128. The example system 100 includes a catheter 102, signal processing device 114, computing device 116 and analysis database 118.

The catheter 102 is configured to detect cardiac activation information in the heart and to transmit the detected cardiac activation information to the signal processing device 114, via a wireless connection, wired connection, or a combination of both wired and wireless connections. The catheter includes a plurality of probes/sensors 104-112, which can be inserted into the heart through the patient's blood vessels. Sensors may detect unipolar and/or bipolar signals from the patient heart 120.

In some embodiments or aspects, one or more of the sensors 104-112 may not be inserted into the patient's heart. For example, some sensors may detect cardiac activation via the patient's surface (e.g., electrocardiogram—ECG) or remotely without contact with the patient (e.g., magnetocardiogram). As another example, some sensors may also derive cardiac activation information from cardiac motion of a non-electrical sensing device (e.g., echocardiogram). In various embodiments or aspects, these sensors can be used separately or in different combinations, and further these separate or different combinations can also be used in combination with sensors inserted into the patient's heart 120.

The sensors 104-112, which are positioned at sensor locations in respect to the heart 120 under consideration, can detect cardiac activation information at the sensor locations and can further deliver energy to ablate the heart at the sensor locations. It is noted that the sensors 104-112 can also detect cardiac activation information from overlapping regions of the heart (e.g., right atrium 122 and left atrium 124).

The catheter 102 can transmit the sensed cardiac activation information of the sensors 104-112 to the signal processing device 114. The signal processing device 114 is configured to process (e.g., clarify and amplify) the cardiac activation information detected by the sensors 104-112 at the sensor locations into electrogram signals and to provide the processed signals to the computing device 116 for analysis in accordance with methods disclosed herein. In processing the cardiac activation information from the sensors 104-112, the signal processing device 114 can subtract cardiac activation information from overlapping regions of the heart 120 to provide processed signals to the computing device 116 for analysis. While in some embodiments or aspects, the signal processing device 114 is configured to provide unipolar signals, in other embodiments, the signal processing device 114 can provide bipolar signals.

The computing device 116 is configured to receive or access the detected and processed signals from the signal processing device 114 and further configured to analyze the signals in accordance with methods disclosed herein to determine at least one spatial area including one or more spatial elements about which there is progressive angular deviation (PAD) of activation (e.g., activation onset times) associated with other spatial elements for a number activation cycles.

The computing device 116 is further configured to generate and display an activation propagation map (APM) video 150, which combines and displays spatially the activation information from a plurality of signals, which may take many forms including monophasic action potential (MAP) signal representations. The APM video 150 includes a sequence of APM frames that are associated with a series of time increments over an analysis time interval (e.g., 4000 msec or another analysis time interval). The arrow 152 indicates rotational movement of the activation information. The spatial elements in the MAP representation are associated with sensors 104 in an array of sensors. The signal (in this case MAP representation) includes voltage (or charge) versus time and other indexes. The signal representation may also include activation onset time information associated with the electrical activity sensed by a sensor 104 of the array of sensors. The MAP representation can be mapped as curves on time and voltage axes, as well as several other representations including polar plots and three-dimensional plots.

As used herein, activation onset time is a time point at which activation commences in a cell or tissue, as opposed to other time points during activation. Activation is a process whereby a cell commences its operation from a quiescent (diastolic) state to an active (electrical) state.

The computing device 116 receives, accesses, or generates the representations of the APM video 150. As an example of the generation of an APM video 150 and representations in the form of monophasic action potentials (MAPs) is described in U.S. Pat. No. 8,165,666, which is incorporated herein by reference in its entirety. In particular, FIG. 11 of the '666 patent illustrates an APM video 150 of MAPs.

Other methods and systems that provide such representations can be used. The APM video 150 may be generated by any other systems and methods that can reconstruct cardiac or biological information over time to generate a dynamic representation of activation information.

The analysis database 118 is configured to support or aid in the analysis of the signals by the computing device 116. In some embodiments, the analysis database 118 can store the AMP video 150, as will be described in greater detail herein. The analysis database 118 can also provide storage of intermediate data (e.g. PAD pairs of spatial elements) associated with the determining one or more areas associated with a heart rhythm disorder.

Figure 2:
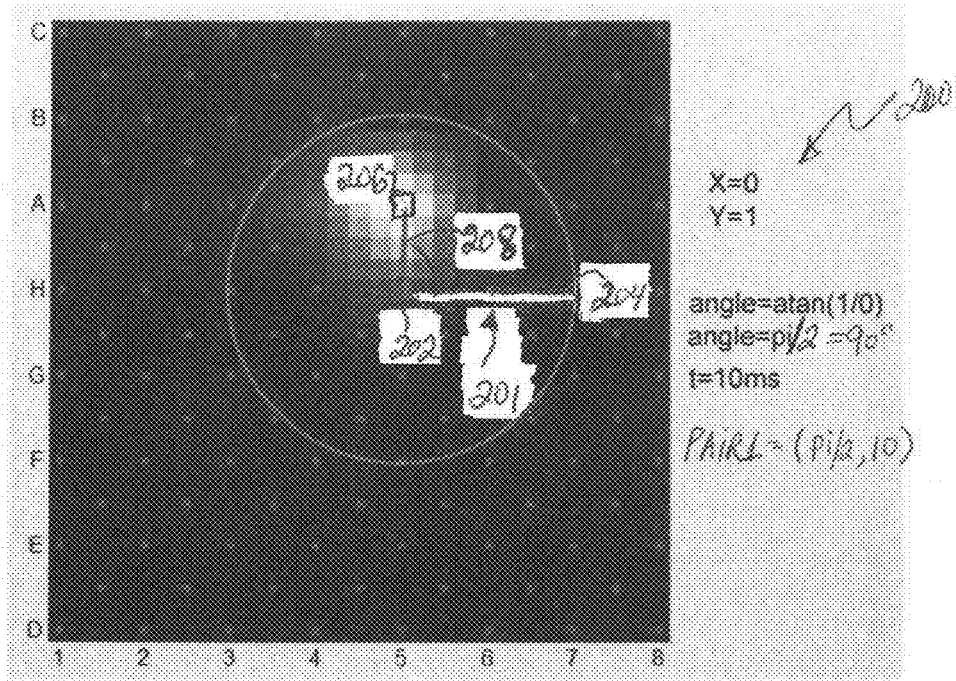
FIG. 2 illustrates one example embodiment for the formation of progressive angular deviations (PADs) in relation to a spatial element.

FIG. 2 illustrates an example frame representation 200 of the APM video 150 (e.g., a monophasic action potential (MAP) as described in U.S. Pat. No. 8,165,666) received, accessed, or generated by the computing device 116. The AMP video 150 identifies activation information for a selected analysis time period (e.g., 4000 msec) associated with a heart rhythm disorder. For illustrative purposes, the frame representation 200 illustrates activation information occurring at a first time point (e.g., 10 msec) of the analysis time interval.

A spatial element 202 associated with a sensor (e.g., indicated in red) is selected for processing in the AMP video 150. It should be noted that one or more of a plurality of spatial elements (e.g., 120 spatial elements) can processed sequentially or in parallel in accordance with the methodology described herein in connection with spatial element 202.

A circle 204 (e.g., indicated in green) having a radius (e.g., two (2) sensor distance) extending from the selected spatial element 202 is determined. The radius is given as an example, and a larger or a smaller radius can be selected. Thereafter, a set including a plurality of sensors 104 on or within the circle 204 is then determined for processing in connection with spatial element 202. It should be noted that a differently dimensioned and/or sized shape can be used (e.g., square, diamond, etc.).

The first time point (10 msec) indicates a first activation onset time of any sensor in the determined set of sensors during the analysis interval of time (e.g., 4000 msec). For example, the activation onset time of 10 msec is associated with a sensor 206. The white line 201 indicates 0 . . . 2pi about the circle 204 in a counterclockwise direction. An angle 208 is determined from the selected spatial element 202 to the associated sensor 206. Thereafter, a pair which includes the angle and the activation time is generated (e.g., Pair 1=(pi/2, 10) for the first activation onset time. It should be notes that one or more additional pairs can be generated for any another sensors in the set that have associated activation onset time at 10 msec.

Figure 3:
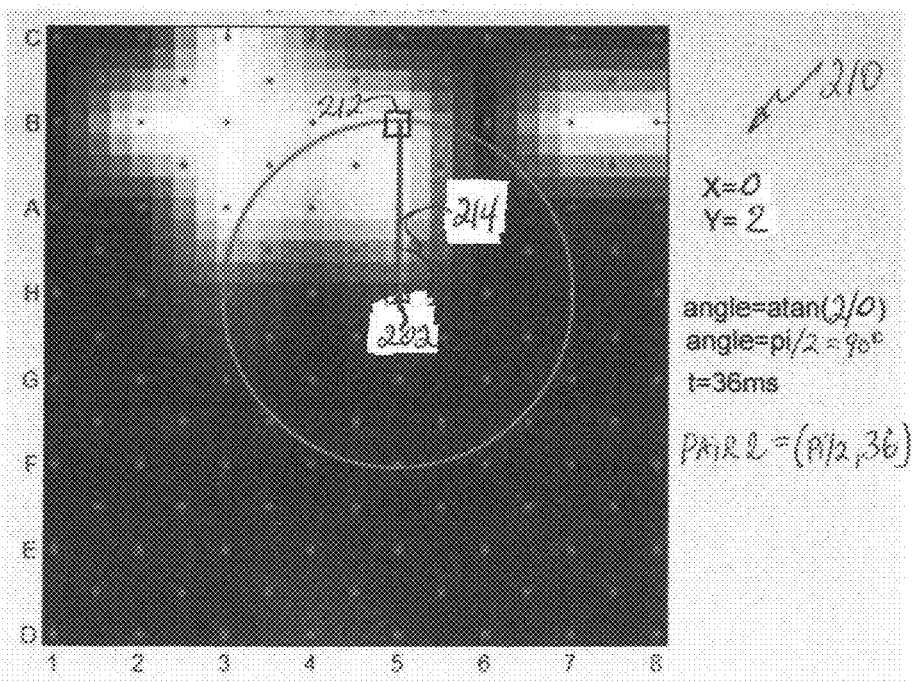
FIG. 3 illustrates another example embodiment for the formation of progressive angular deviations (PADs) in relation to a spatial element.

FIG. 3 illustrates an example frame representation 210 of the APM video 150 received, accessed, or generated by the computing device 116. For illustrative purposes, the frame representation 210 illustrates activation information occurring at a second time point (e.g., 36 msec) of the analysis time interval (e.g., 4000 msec).

The second time point (36 msec) indicates a second activation onset time of any sensor in the determined set of sensors during the analysis interval of time (e.g., 4000 msec). For example, the activation onset time of 36 msec is associated with a sensor 212. An angle 214 is determined from the selected spatial element 202 to the associated sensor 212. Thereafter, a pair which includes the angle and the activation time is generated (e.g., Pair 2=(pi/2, 36) for the second activation onset time. It should be notes that one or more additional pairs can be generated for any another sensors in the set that have associated activation onset time at 36 msec.

Figure 4:
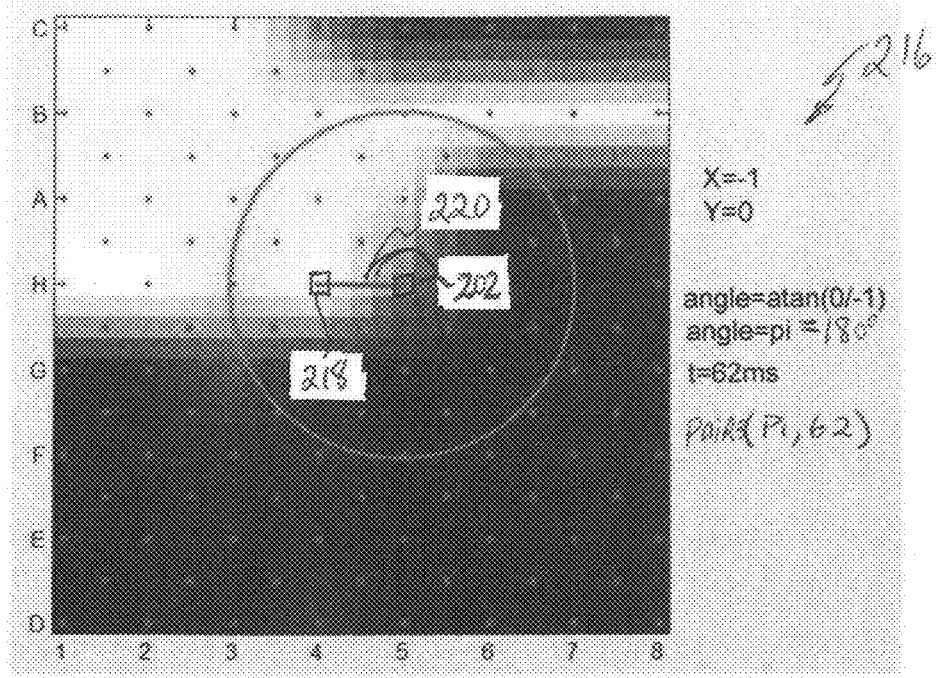
FIG. 4 illustrates still another example embodiment for the formation of progressive angular deviations (PADs) in relation to a spatial element.

FIG. 4 illustrates an example frame representation 216 of the APM video 150 received, accessed, or generated by the computing device 116. For illustrative purposes, the frame representation 216 illustrates activation information occurring at a third time point (e.g., 62 msec) of the analysis time interval (e.g., 4000 msec).

The third time point (62 msec) indicates a third activation onset time of any sensor in the determined set of sensors during the analysis interval of time (e.g., 4000 msec). For example, the activation onset time of 62 msec is associated with a sensor 218. An angle 220 is determined from the selected spatial element 202 to the associated sensor 218. Thereafter, a pair which includes the angle and the activation time is generated (e.g., Pair 3=(pi, 62) for the third activation onset time. It should be notes that one or more additional pairs can be generated for any another sensors in the set that have associated activation onset time at 62 msec.

Figure 5:
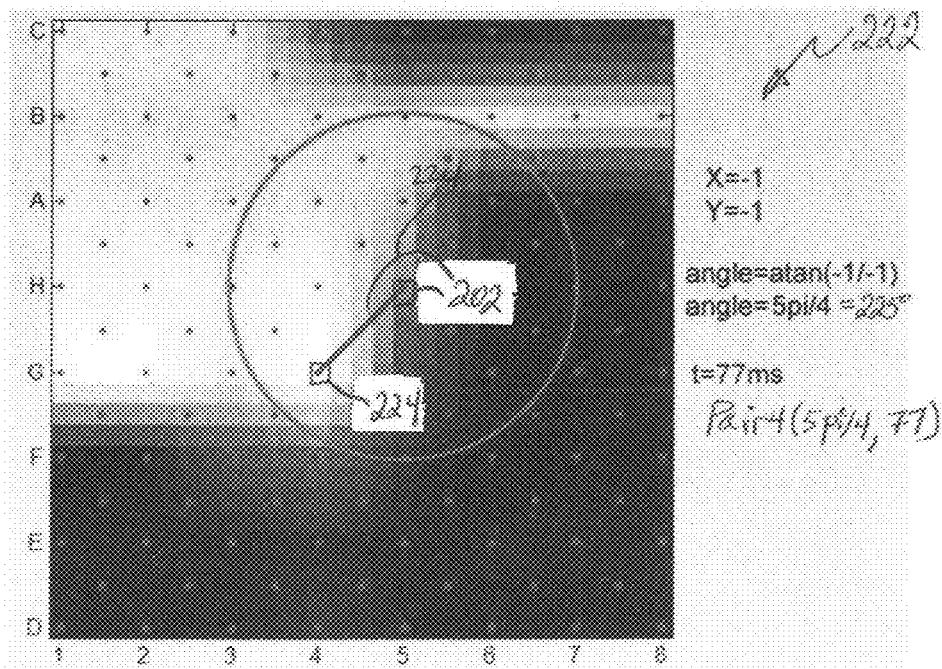
FIG. 5 illustrates yet another example embodiment for the formation of progressive angular deviations (PADs) in relation to a spatial element.

FIG. 5 illustrates an example frame representation 222 of the APM video 150 received, accessed, or generated by the computing device 116. For illustrative purposes, the frame representation 222 illustrates activation information occurring at a fourth time point (e.g., 77 msec) of the analysis time interval (e.g., 4000 msec).

The fourth time point (77 msec) indicates a third activation onset time of any sensor in the determined set of sensors during the analysis interval of time (e.g., 4000 msec). For example, the activation onset time of 77 msec is associated with a sensor 224. An angle 224 is determined from the selected spatial element 202 to the associated sensor 224. Thereafter, a pair which includes the angle and the activation time is generated (e.g., Pair 4=(5pi/4, 77) for the fourth activation onset time. It should be notes that one or more additional pairs can be generated for any another sensors in the set that have associated activation onset time at 77 msec.

For illustrative purposes, FIGS. 2-5 detail four (4) example frames representations of activation onset times, associated with sensors in the determined set of sensors, occurring during the analysis interval of time (e.g., 4000 msec). However, it should be noted that there could be significantly more activation onset times associated with sensors in the determined set during the analysis time interval (e.g., 4000 msec).

Figure 6:
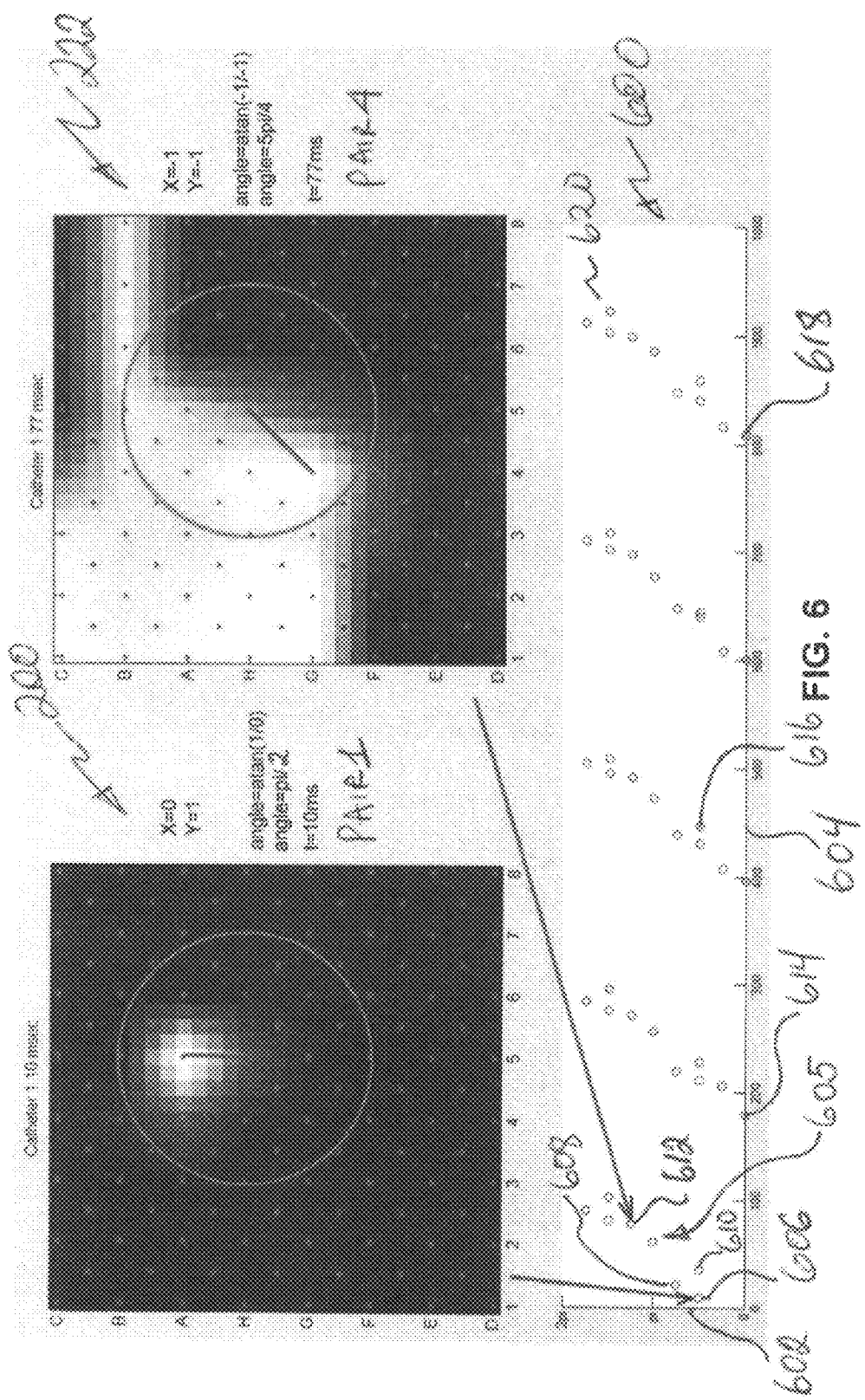
FIG. 6 illustrates a first correlation of PADs in an analysis time interval, with example frame representations inset.

FIG. 6 illustrates a graphical representation 600 of the generated pairs 605. The graphical representation 600 illustrates the generated pairs 605 plotted on a time-angle graph, i.e., angle 602, time 604. As an example, pair 1 (pi/2, 10) of frame representation 200 is plotted as pair 606 and pair 4 (5pi/4, 77) of frame representation 222 is plotted as pair 612. It should be noted that the graphical representation 600 illustrates a plurality of generated pairs 605, such a pairs 606-620, which are shown for illustrative purposes.

Figure 7:
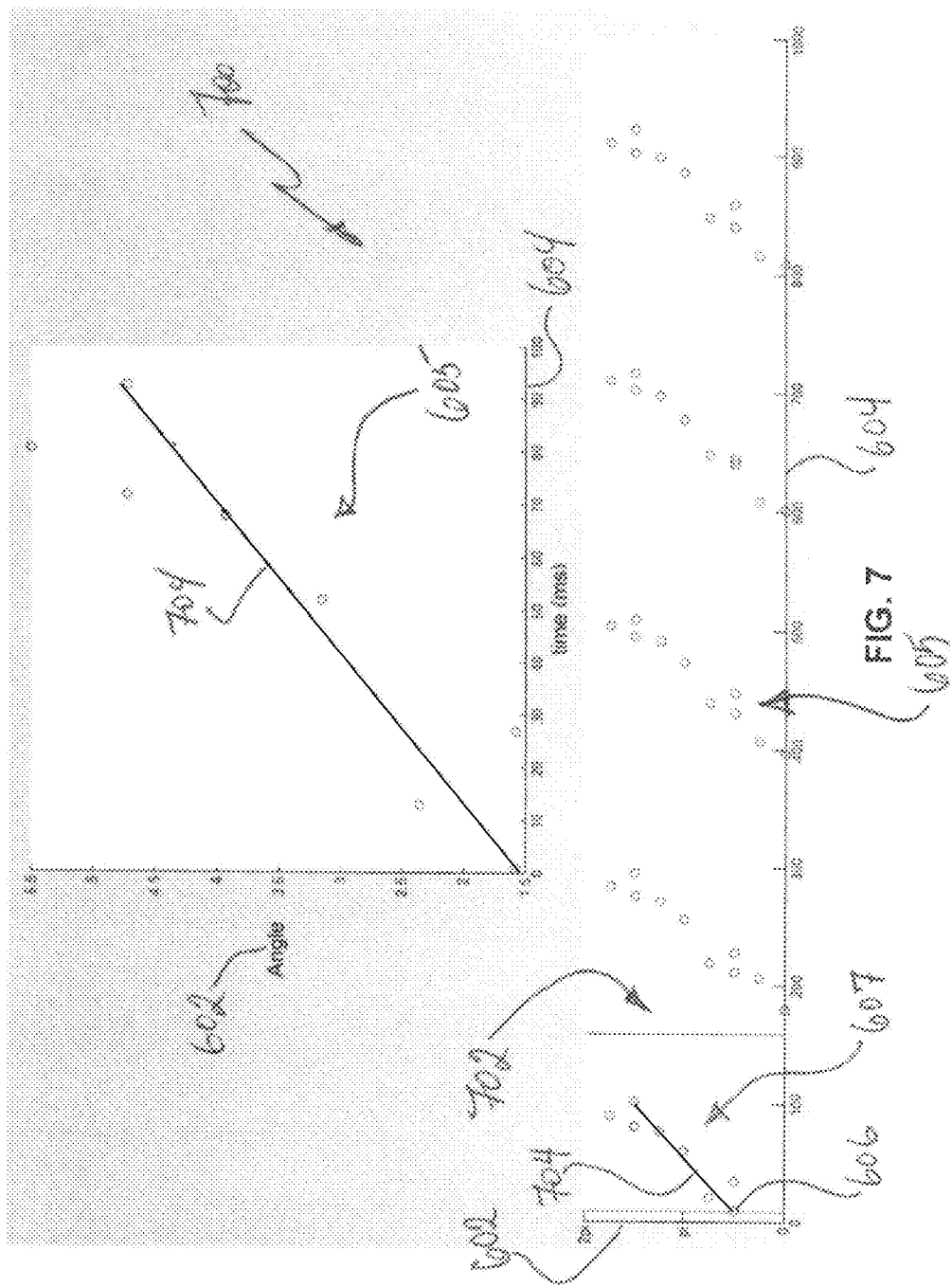
FIG. 7 illustrates a first correlation of PADs in an analysis time interval with a calculated best-fit-line.

FIG. 7 illustrates a graphical representation 700 showing the calculation of lines that best fit pairs of the plurality of pairs 605 in a window 702 (e.g., first window) anchored at a first pair 606. A size of the first window 702 is defined to be a predetermined percentage (e.g., 75%) of a cycle length that is determined to be associated with the heart rhythm disorder. It should be noted that the cycle length associated with the heart rhythm disorder can be a median cycle length, an average length, or another threshold cycle length that is determined in connection with the heart rhythm disorder.

Determination of the size of the first window 702 can vary with the specific rhythm disorder. In general, a short window restricts a complete definition of the rotational/focal activation. Conversely, a long window—such as the entire cycle—can result in a failure to detect a cycle if there are small accelerations of rate in preceding beats (e.g., faster beats). The more regular ('simple') the rhythm disorder, the smaller the proportion of the cycle length that can be required in order to establish a rotational pattern. In a complex rhythm disorder, such as atrial fibrillation, one embodiment can typically select >50% of the cycle length as the window duration over which to establish rotational activation. This precise size of the first window 702 can be tailored to a specific patient, and retained in a database for reuse, e.g., should the patient have a repeat procedure.

For example, the cycle length associated with the heart rhythm disorder is determined to be 200 msec. Accordingly, the size of the first window is 150 msec (e.g., 200 msec*75%=150 msec). A different percentage may be selected. The first window 702 is anchored at the first pair 606 of the plurality of pairs 605. A best-fit-line 704 is calculated in reference to the pairs 607 of the plurality of pairs 605 that fall on or within the first window 702. Various algorithms can be used to determine the best-fit-line 704, based on minimizing mean-square-error of the deviation of each pair from a linear regression, or a weighted mean-square-error line.

The slope of the best-fit-line 704, location of the best-fit-line 704 (e.g., middle of line) and a metric of the fit of the pairs to the best-fit-line 704 are calculated and recorded in association with the calculated best-fit-line 704. The fit of the pairs to the best-fit-line 704 can be determined by a root-mean-squared-error (RMSE) calculation, or another algorithm that can provide a metric of how closely the pairs fit the best-fit-line 704. The first window 702 is advanced and anchored to a successive pair as illustrated in FIG. 8.

Figure 8:
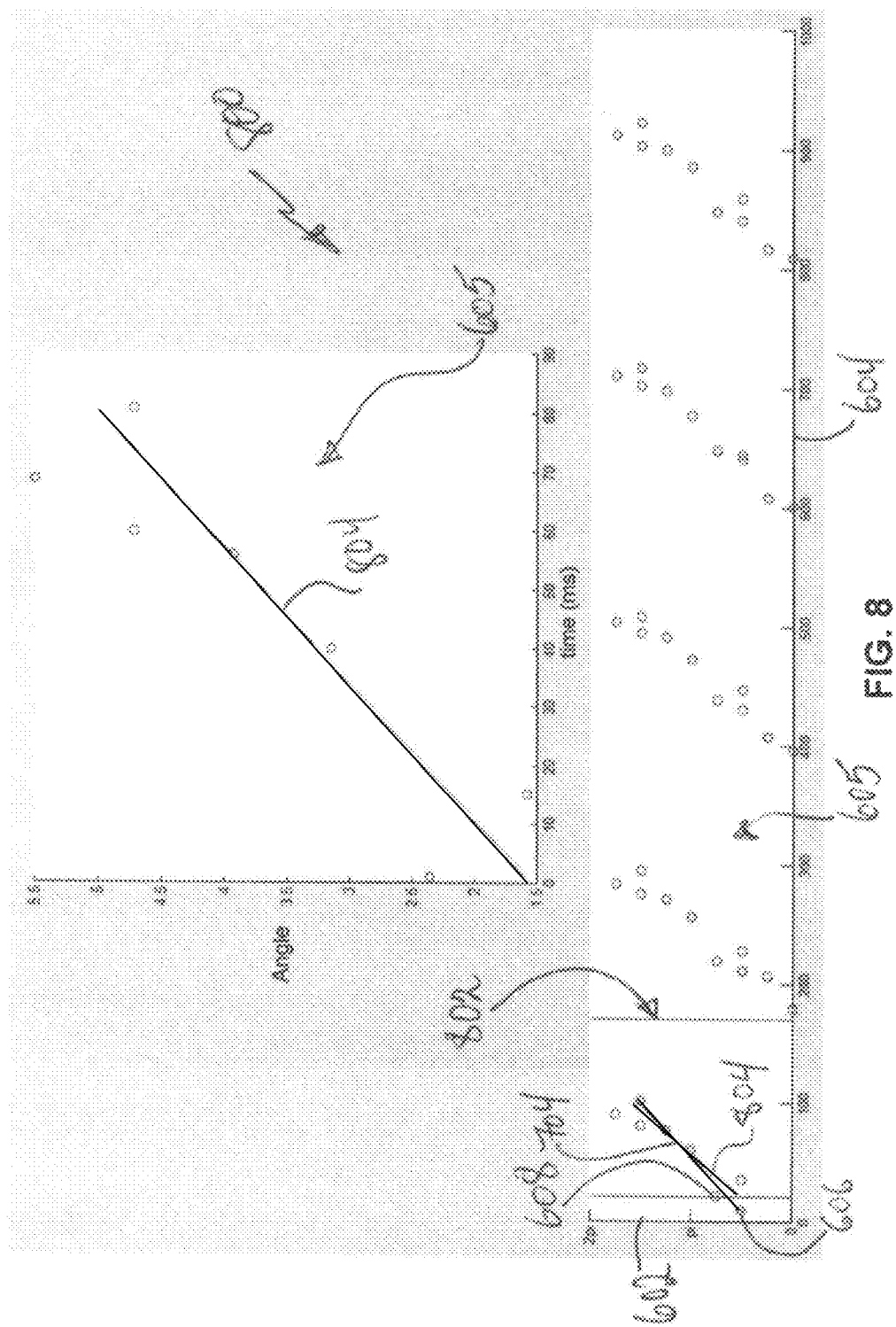
FIG. 8 illustrates an exemplary correlation of PADs using a first time window in an analysis time interval.

FIG. 8 illustrates a graphical representation 800 showing the calculation of lines that best fit pairs of the plurality of pairs 605 in a window 802 (also considered a first window) anchored at a second pair 608. The first window 802 is of the first size, e.g., 150 msec (75% of 200 msec cycle length associated with the heart rhythm disorder).

The first window 802 is anchored at the second pair 608 of the plurality of pairs 605. A best-fit-line 804 is calculated in reference to the pairs that fall on or within the window 802. The slope of the best-fit-line 802, location of the best-fit-line 804 (e.g., middle of line) and a metric of the fit of the pairs to the best-fit-line 804 are calculated and recorded in association with the calculated best-fit-line 804. The first window 802 is advanced and anchored to a successive pair as illustrated in FIG. 9.

Figure 9:
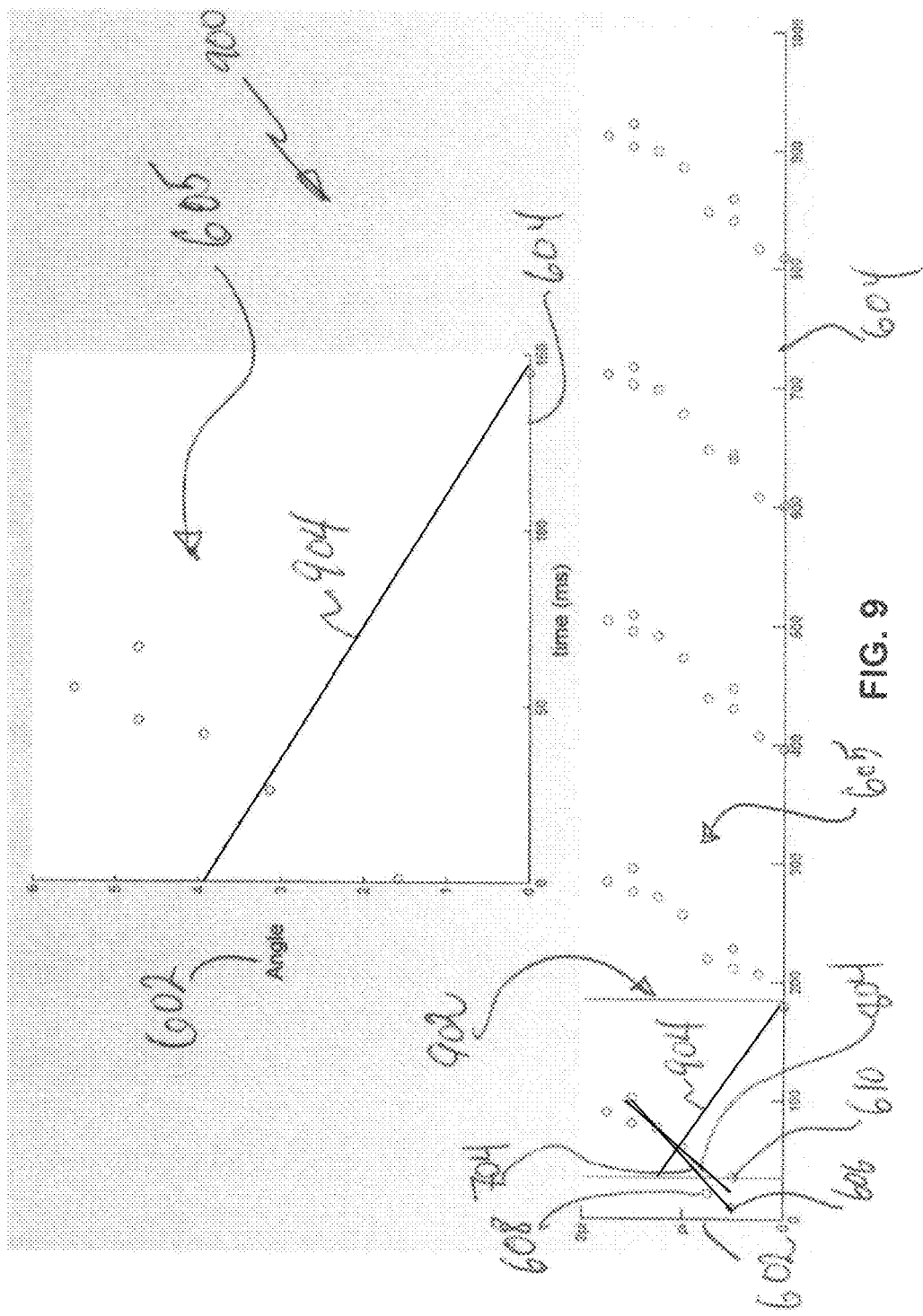
FIG. 9 illustrates another correlation of PADs using a first time window in an analysis time interval.

FIG. 9 illustrates a graphical representation 900 showing the calculation of lines that best fit pairs of the plurality of pairs 605 in a window 902 (also considered a first window) anchored at a third pair 610. The window 902 is of the first size, e.g., 150 msec (75% of 200 msec cycle length associated with the heart rhythm disorder).

The first window 902 is anchored at the third pair 610 of the plurality of pairs 605. A best-fit-line 904 is calculated in reference to the pairs that fall on or within the first window 902. The slope of the best-fit-line 904, location of the best-fit-line 904 (e.g., middle of line) and a metric of the fit of the pairs to the best-fit-line 904 are calculated and recorded in association with the calculated best-fit-line 802. The first window 902 is advanced and anchored to a successive pair as illustrated in FIG. 9.

Figure 10:
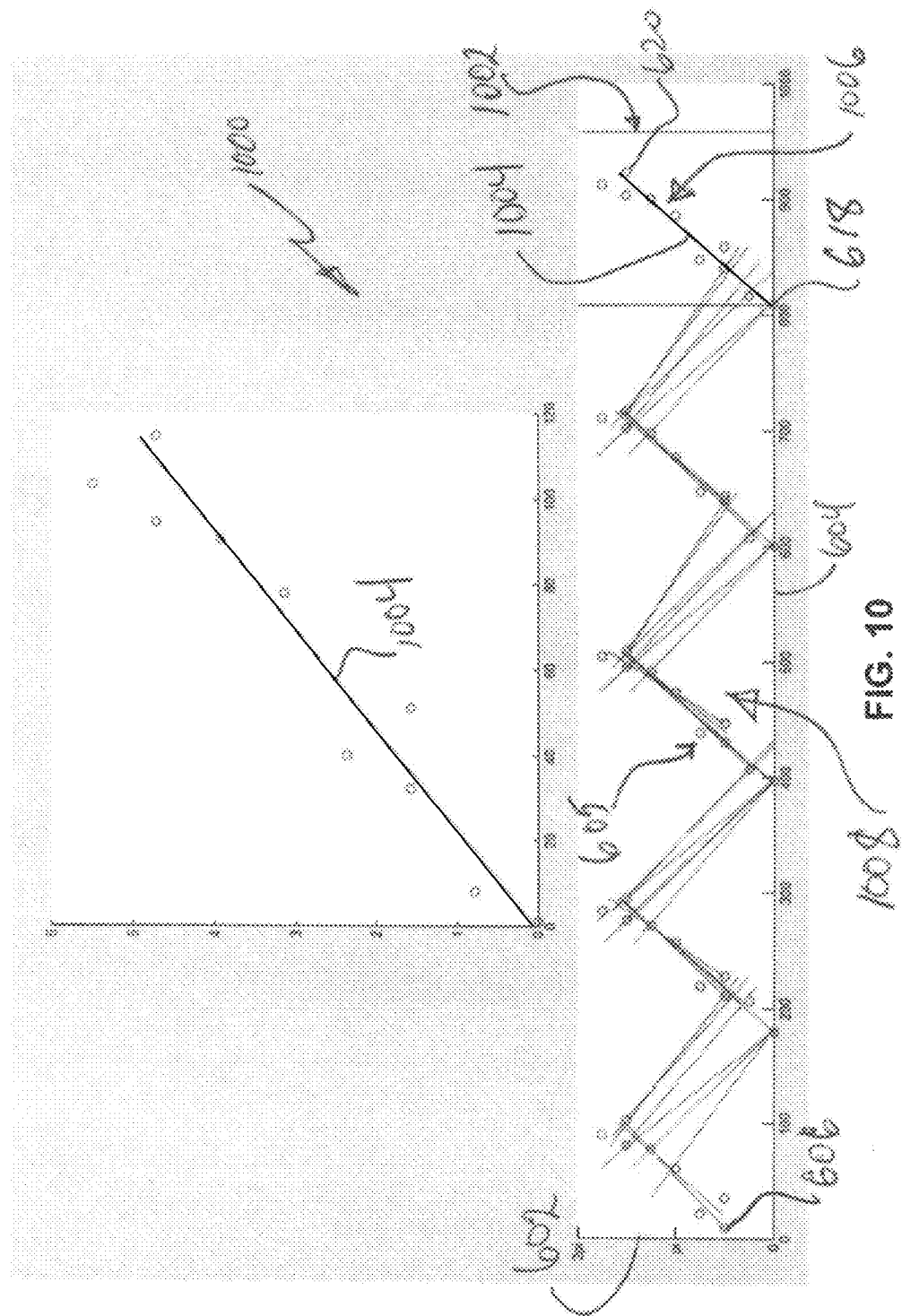
FIG. 10 illustrates still another correlation of PADs using a first time window in an analysis time interval

FIG. 10 illustrates a graphical representation 1000 showing the calculation of lines that best fit pairs of the plurality of pairs 605 in $n^{th}$ window 1002 (also considered a first window) anchored at an $n^{th}$ pair 618. The first window 1002 is of the first size, e.g., 150 msec (75% of 200 msec cycle length associated with the heart rhythm disorder).

The first window 1002 is anchored at the $n^{th}$ pair 618 of the plurality of pairs 605. A best-fit-line 1004 is calculated in reference to the pairs 1006 that fall on or within the first window 1002. For example, the $n^{th}$ window 1002 will include pairs 1006 of pairs 605 that remain to be processed for the relevant analysis time interval. The slope of the best-fit-line 1004, location of the best-fit-line 1004, (e.g., middle of line) and a metric of the fit of the pairs to the best-fit-line 1004, are calculated and recorded in association with the calculated best-fit-line 1004.

As illustrated in FIGS. 7-10, the first window of the first size is successively advanced and anchored to successive pairs of the plurality of pairs 605 between the first pair 606 and the $n^{th}$ pair 618 until all pairs 605 are processed in the analysis time interval, which generates a plurality of best-fit-lines 1008, as illustrated in FIG. 10.

Figure 11:
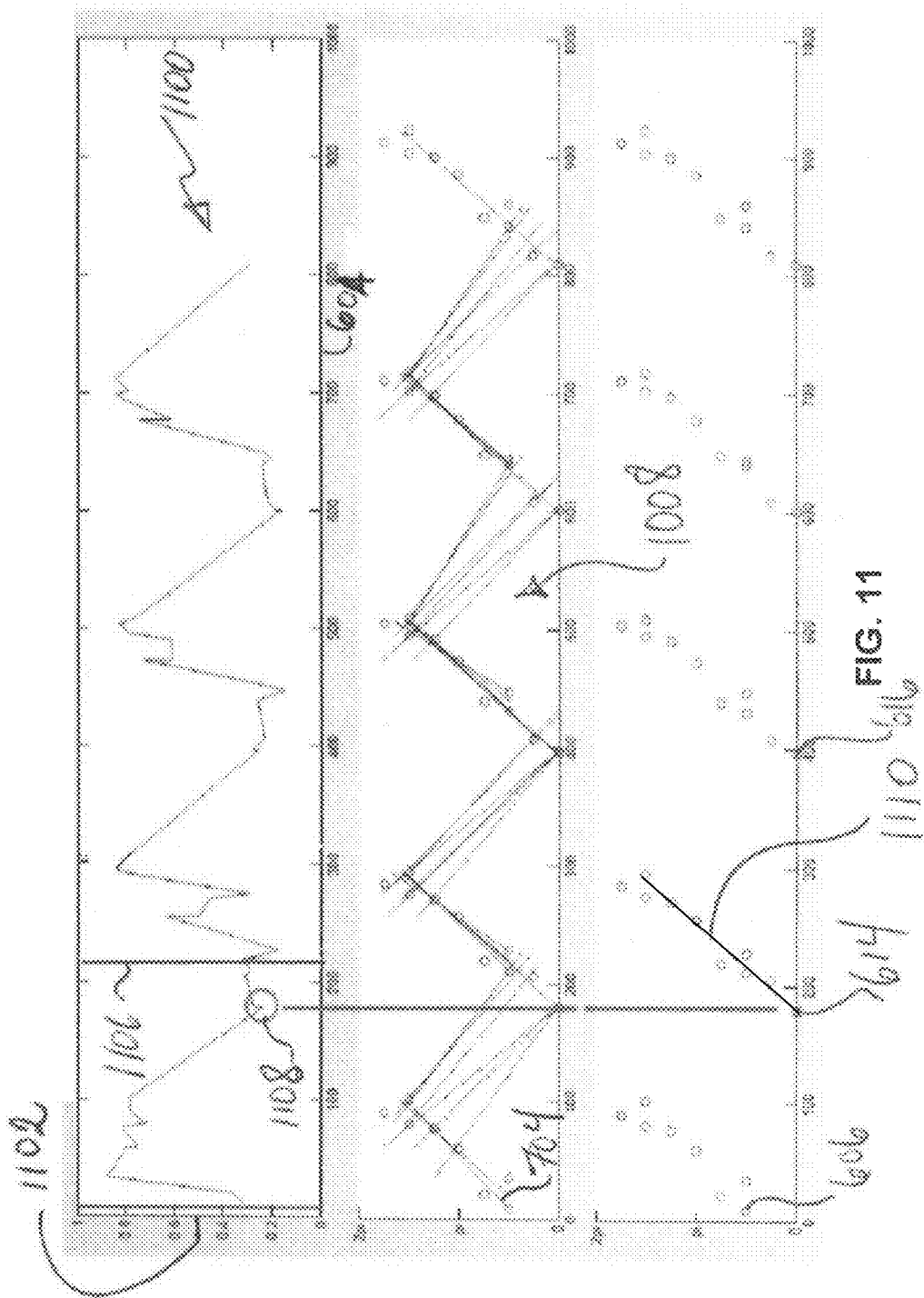
FIG. 11 illustrates an example second correlation of PADs using a second time window in an analysis time interval.

FIG. 11 illustrates a graphical representation 1000 showing selection of a line that best fits pairs of the plurality of pairs 605 in a window 1106 (e.g., second window) anchored at a first pair 606. A size of the second window 1106 is defined to be a predetermined percentage (e.g., 110%) of a cycle length that is associated with the heart rhythm disorder. A different percentage may be selected.

In the foregoing example, the cycle length determined to be associated with the heart rhythm disorder is 200 msec. Accordingly, the size of the second window is 220 msec (e.g., 200 msec*110%=220 msec). The second window 1106 is anchored at the first pair 606 of the plurality of pairs 605. The best-fit-line 1110 is then selected within the second window 1106. For example, the fit (e.g., minimal error) of the pairs to the best-fit lines can be used to select the best-fit-line 1110 in the second window 1106.

As an example, a root-mean-squared-error (RMSE) can be used as a metric for the selection of the best-fit line 1110. Specificity, the RMSE enables selection of a best-fit line 1110 in connection with which minimal error (metric) 1108 of the pairs to the associated best-fit line. It should be noted that various other algorithms, and combinations of mentioned algorithm and/or other algorithms, can be used to select the best-fit-line 1110. The second window 1106 is advanced and anchored to line after the window as illustrated in FIG. 12.

Figure 12:
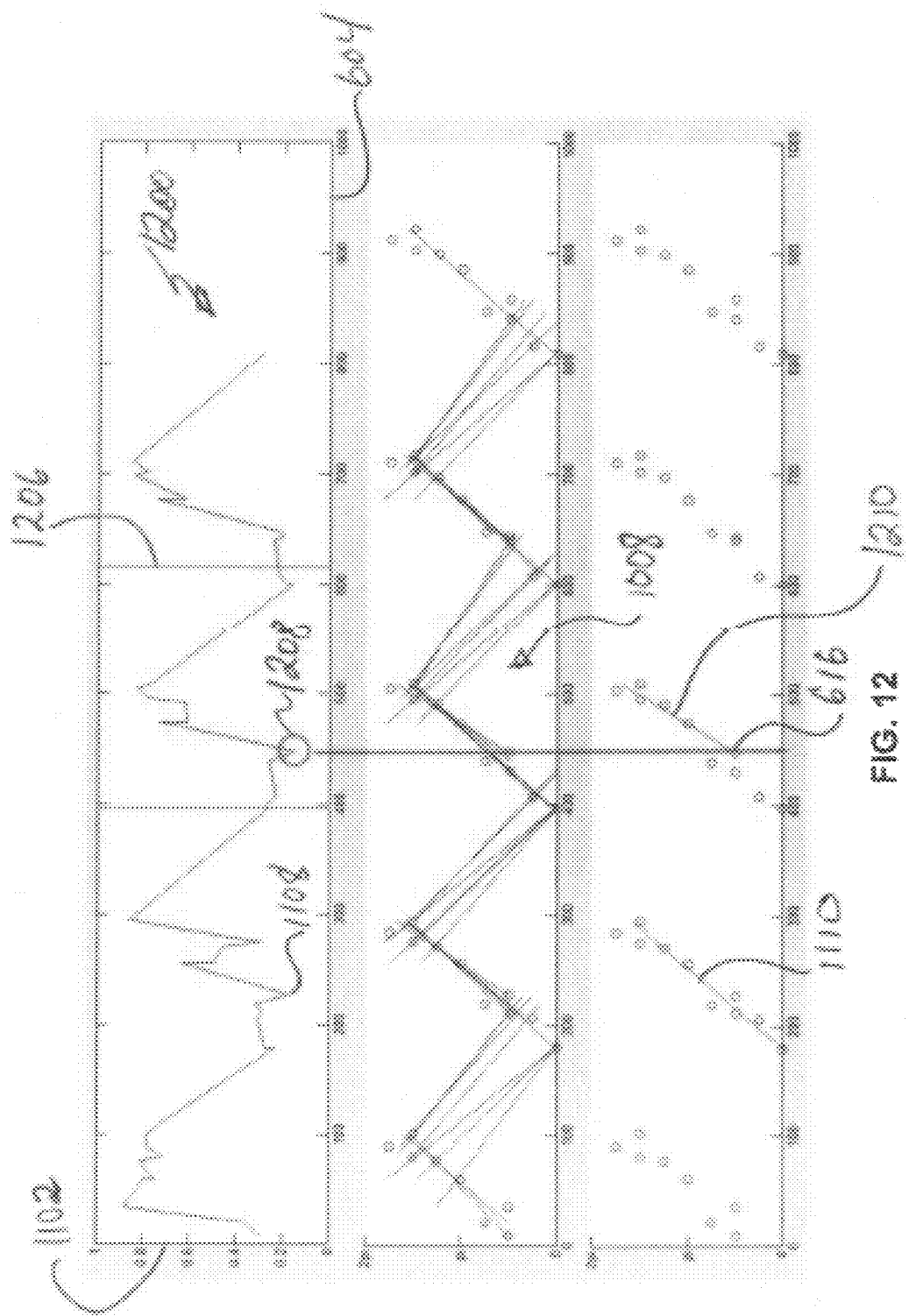
FIG. 12 illustrates another example second correlation of PADs using a second time window in an analysis time interval.

FIG. 12 illustrates a graphical representation 1200 showing selection of a line that best fits pairs of the plurality of pairs 605 in a window 1206 (also considered a second window) anchored at a first best-fit line after the first window 1106.

In the foregoing example, the cycle length that is determined to be associated with the heart rhythm disorder is 200 msec. Accordingly, the size of the second window is 220 msec (e.g., 200 msec*110%=220 msec). The second window 1106 a best-fit line after the second window 1106 that is anchored at pair 616 of the plurality of pairs 605. Specifically, the anchor pair 614 of the selected best-fit line 1110 occurs at approximately 180 msec. Thereafter, half of the determined cycle length of 110 msec (e.g., 220 msec*0.5) is added to the time of 180 msec, which is a total of 290 msec. The half-cycle is added as a 'blanking period' such that the next analysis window does not overlap with the terminal portion of the current analysis window. The first best-fit line after the 290 msec is anchored at pair 616 occurring approximately at 400 msec because no other data pairs are available between approximately 290 msec and 400 msec. Accordingly, the second window 1206 extends from approximately 400 to approximately 620.

The best-fit-line 1210 is then selected within the second window 1206. For example, the fit (e.g., minimal error) of the pairs to the best-fit lines can be used to select the best-fit-line 1210 in the second window 1206.

As an example, a root-mean-squared-error (RMSE) can be used as a metric for the selection of the best-fit line 1210. Specificity, the RMSE enables selection of a best-fit line 1210 in connection with which minimal error (metric) 1208 of the pairs to the associated best-fit line. As described before, various other algorithms, and combinations of mentioned algorithm and/or other algorithms, can be used to select the best-fit-line 1210.

As illustrated and described in reference to FIGS. 11 and 12, the second window of the second size is successively advanced and anchored to the first best-fit line after the second window 1106, until all best-fit lines are processed in the analysis time interval.

Figure 13:
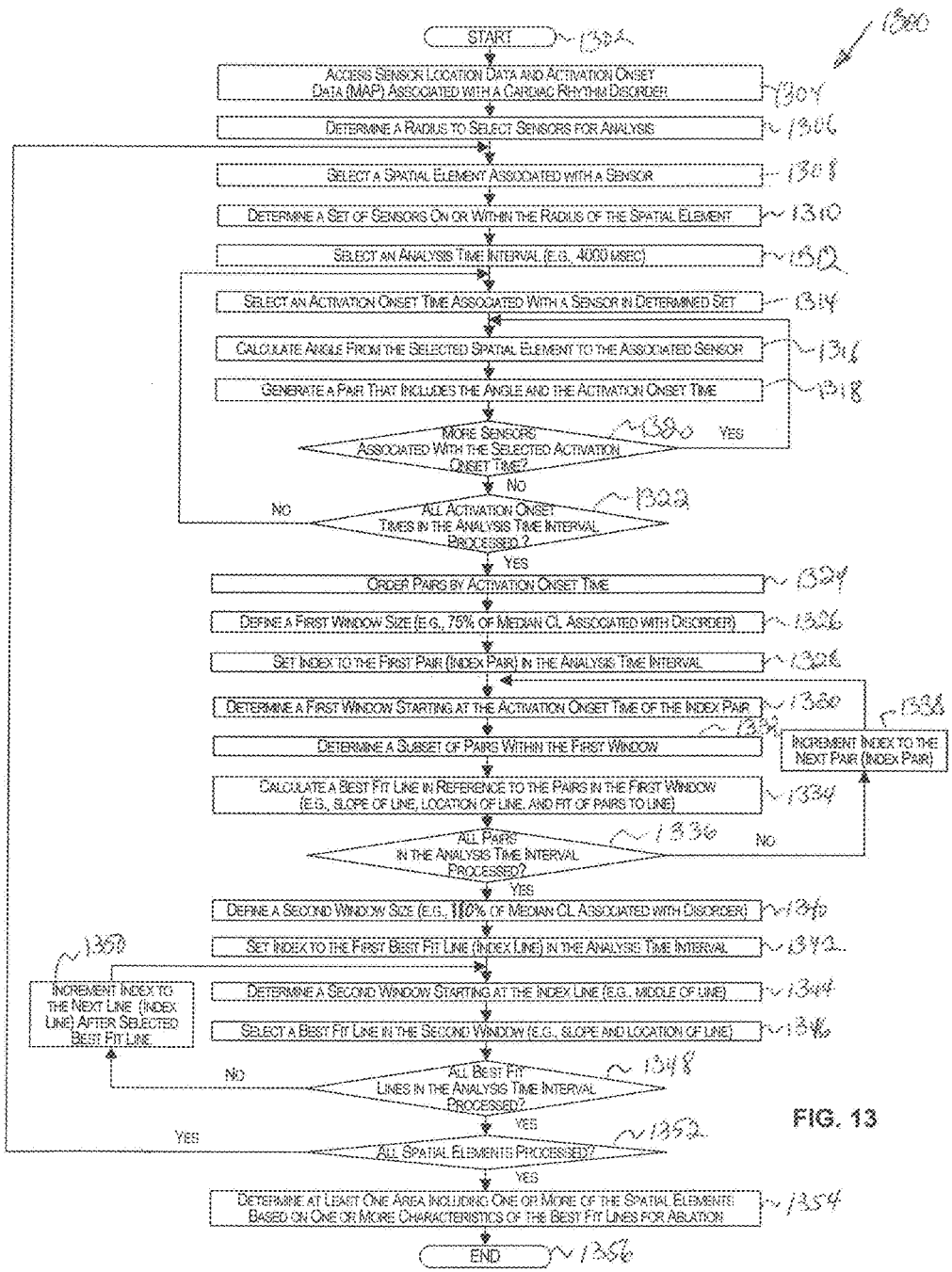
FIG. 13 illustrates a method of determining and correlating progressive angular deviations (PADs) in connection to a spatial elements.

FIG. 13 is a flowchart of an example method 1300 of determining an area of one or more spatial elements that are related to progressive angular deviations of activation onset times. The method starts at operation 1302. At operation 1304, the method 1300 accesses location data and activation onset data in connection with a heart rhythm disorder (e.g., the monophasic action potential data from (MAP) representations of the signals, e.g., APM video 150). The MAP representation includes sensor.

At operation 1306, a radius (e.g., FIG. 2, radius 204) is determined for the selection of sensors in connection with a spatial element. At operation 1308, a spatial element associated with a sensor is selected (e.g., FIG. 2, spatial element 202). Thereafter, a set of sensors on or within the radius of the spatial element is determined at operation 1310.

At operation 1312, an analysis time interval is selected (e.g., 4000 msec). It should be noted that different analysis time intervals can be selected, e.g., longer or shorter than 4000 msec. At operation 1314, an activation onset time associated with a sensor in the determined set is selected. It is noted that this represents a first activation onset time (e.g., in the analysis time interval) associated with any sensor in the determined set of sensors within the radius from the spatial element.

At operation 1316, an angle is calculated from the selected spatial element to the sensor associated with the activation onset time. Thereafter, at operation 1318, a pair of values referred to as "pair") is generated. The generated pair includes the angle and the activation onset time. At operation 1320 a determination is made as to whether there any more sensors associated with the selected activation onset time. If so, the method 1300 iterates over operations 1314-1320 to generate additional pairs (e.g., pair=[angle, activation onset time]) for those sensors. If not, the method 1300 continues at operation 1322.

At operation 1322, a determination is made as to whether all activation onset times in the analysis time interval (e.g., 4000 msec) have been processed. If not, the method 1300 iterates over operations 1314-1322 to generate pairs associated with activation of the sensors in the set over the analysis time interval. If so, the method 1300 continues at operation 1324.

At operation 1324, the generated pairs are ordered by activation onset time. At operation 1326, a first window size is defined in connection with a cycle length associated with the heart rhythm disorder. For example, the first window size can be a selected percentage (e.g., 75%) smaller than the cycle length (e.g., 200 msec) associated with the heart rhythm disorder. Accordingly, the first window size can be defined to be 200 msec*75%=150 msec.

At operation 1328, an index is defined and set to the first pair (e.g., index pair) in the analysis time interval (e.g., 4000 msec). At operation 1330, a first window of the first window size is determined as starting from the activation onset time of the index pair. Thereafter, a subset of all pairs that is within the first window is determined at operation 1332. At operation 1334 a best-fit line is calculated in reference to the subset of pairs in the first window. The slope of the best-fit line, location of the best-fit line, and fit of the pairs to the best-fit line are determined.

At operation 1336, a determination is made as to whether all pairs in the analysis time interval (e.g., 4000 msec) have been processed. If not, the method 1300 continues at operation 1338 to increment the index to the next pair (index pair), and iterates over operations 1330-1336 until all pairs all pairs in the analysis time interval have been processed. If so, the method 1300 continues at operation 1340.

At operation 1340, a second window size is defined in connection with a cycle length associated with the heart rhythm disorder. For example, the second window size can be a selected percentage (e.g., 110%) higher than the cycle length (e.g., 200 msec) associated with the heart rhythm disorder. Accordingly, the second window size can be defined to be 200 msec*110%=220 msec.

At operation 1342, an index is defined and set to the first best-fit line (e.g., index line) in the analysis time interval (e.g., 4000 msec). At operation 1344, a second window of the second window size is determined starting from the index line (e.g., a pair associated with the index line). The pair that is associated with index line can represent the beginning pair of the index line, another other pair, or some point along the index line. Thereafter, a best-fit line out of a plurality of best-fit lines is selected within the second window at operation 1346.

At operation 1348, a determination is made as to whether all best-fit lines in the analysis time interval (e.g., 4000 msec) have been processed. If not, the method 1300 continues at operation 1350 to increment the index to the next index line, and iterates over operations 1344-1348 until all best-fit lines in the analysis time interval have been processed. If so, the method 1300 continues at operation 1352.

At operation 1352, a determination is made as to whether all spatial elements have been processed. If not, the method 1300 iterates over operations 1308-1352 until progressive angular deviations of activation onset times in relation to all spatial elements have been considered. At operation 1354, at least one area having one of more of the spatial elements is determined based on one or more characteristics of the selected best-fit lines, such as that the area can be ablated to ameliorate the heart rhythm disorder. The method end at operation 1356.

Figure 14:
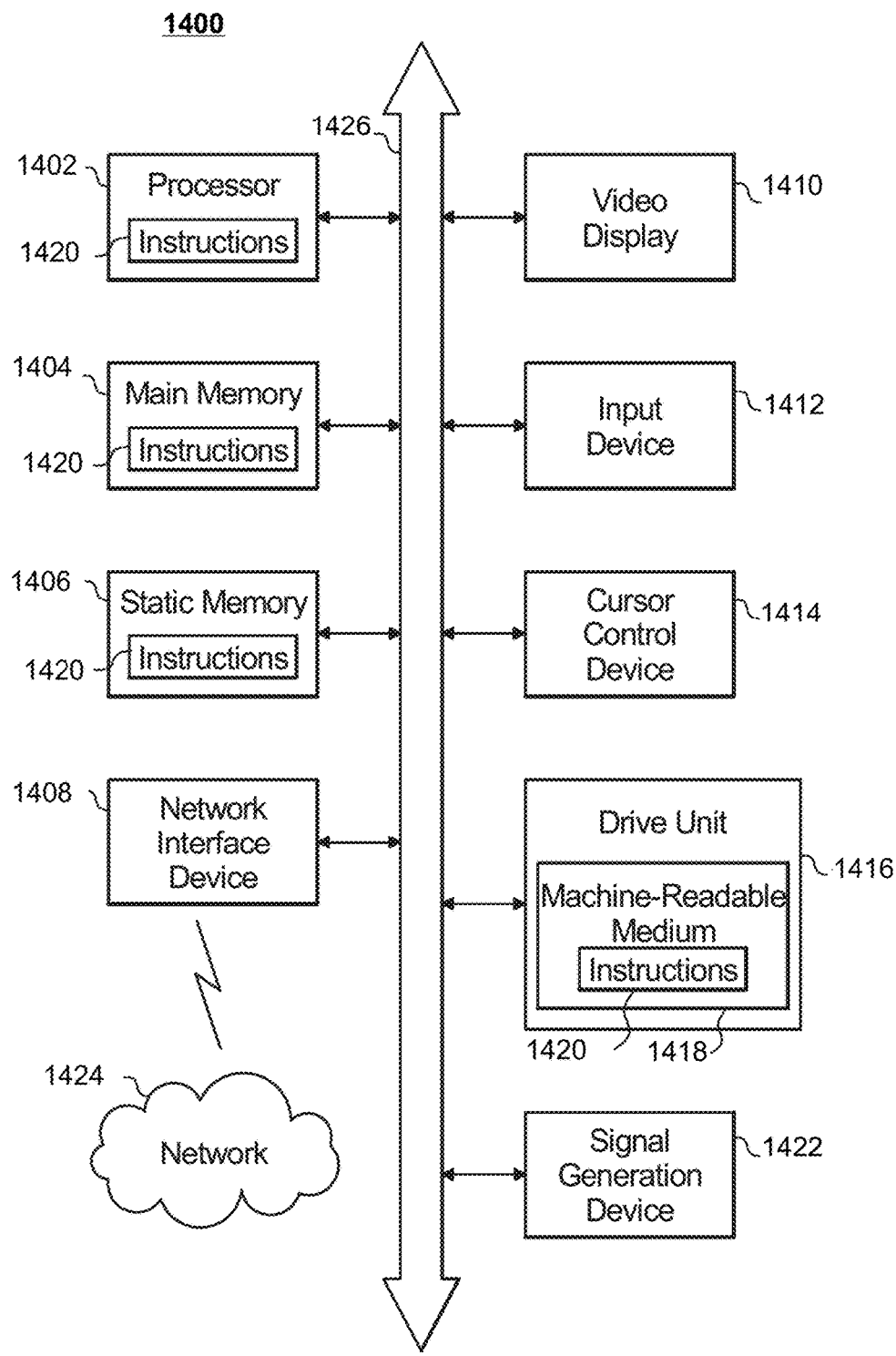
FIG. 14 illustrates a general computing system to perform one or more methods or functionalities disclosed herein.

FIG. 14 illustrates a general computer system that can be used to perform any one or more methods and/or computer based functions described herein. The description of FIG. 14 is provided below, after the description of FIG. 32.

Figure 15:
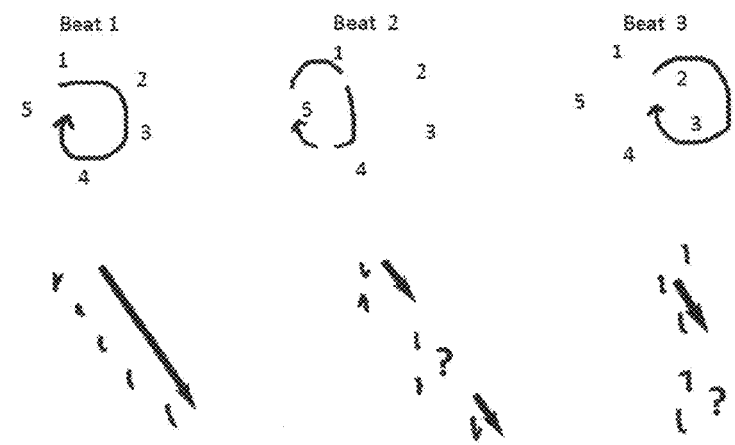
FIG. 15 illustrates example precession of a rotating source (locus) of a complex heart rhythm disorder, and how this will prevent detection of rotation at fixed electrodes using classical methods.

FIG. 15 illustrates an example precession of a rotating source (locus) of a complex heart rhythm disorder. It should be noted that precession of the rotating source will prevent detection of rotation at fixed electrodes using classical methods.

Figure 16:
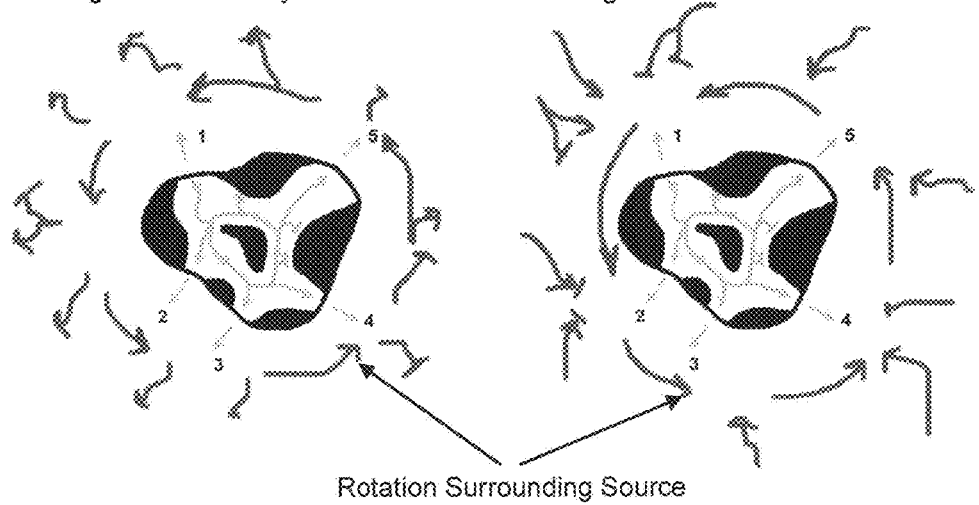
FIG. 16 indicates disorganization that does not disturb the source. (1) Fibrillatory conduction, i.e., disorganization away from the center of the source. (2) Peripheral disorganized activation towards the center of the source that does not perturb the central elements of the source.

FIG. 16 indicates disorganization that does not disturb the source. In section (1), there is shown fibrillatory conduction, i.e., disorganization away from the center of the source. In section (2), there is shown outside disorganization, i.e., peripheral disorganized activation towards the center of the source that does not perturb the central elements of the source.

Figure 17:
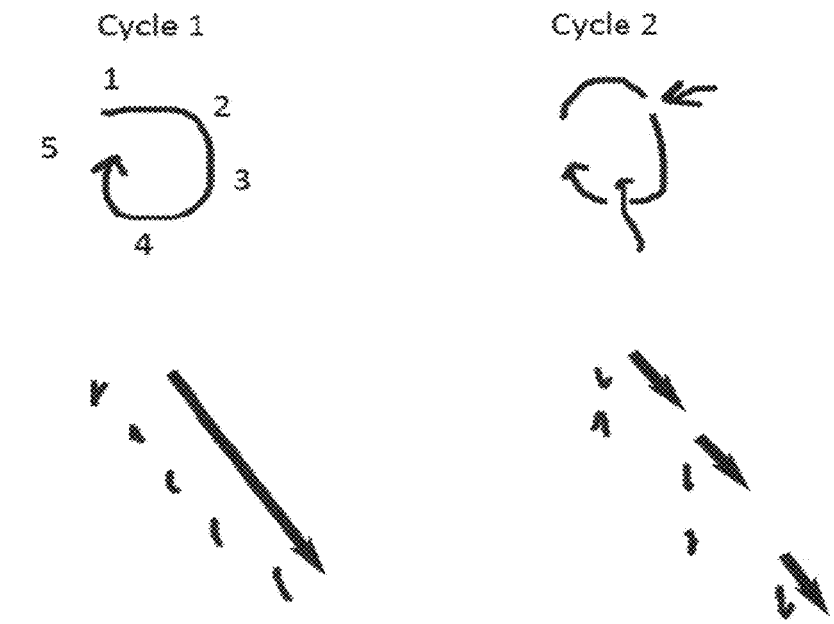
FIG. 17 illustrates the concept of interruption of peripheral portions of a source, for instance, interruption of the rotating spiral arms around a rotor source, by disordered activation. This will prevent detection of sequential rotational activation at fixed electrodes using classical methods of activation mapping, isopotential mapping, or isochronal analysis.

FIG. 17 illustrates the concept of interruption of peripheral portions of a source, for instance, interruption of the rotating spiral arms around a rotor source, by disordered activation. This will prevent detection of sequential rotational activation at fixed electrodes using classical methods of activation mapping, isopotential mapping, or isochronal analysis.

Figure 18:
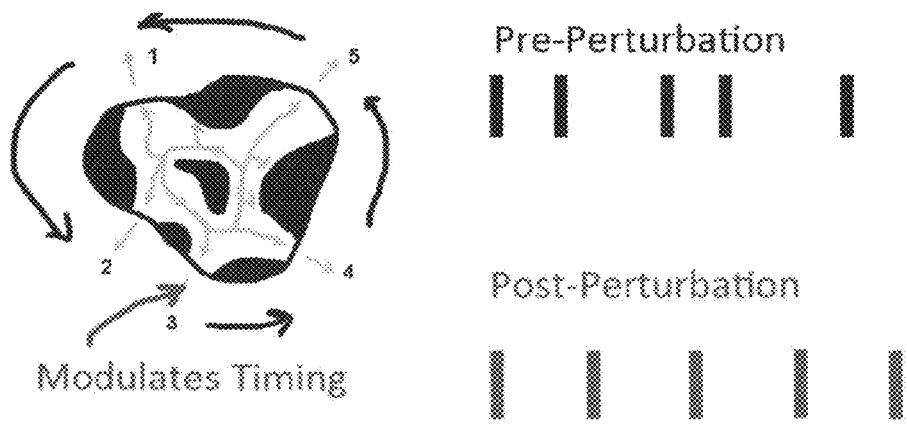
FIG. 18 indicates disorganization that perturbs the rate/regularity of a source. As illustrated, the disorganization constrains irregularity, making it more regular. The opposite may also occur.

FIG. 18 indicates disorganization that perturbs the rate/regularity of a source. As illustrated in FIG. 18, the disorganization constrains irregularity, making it more regular. The opposite of this may also occur.

FIG. 19 indicates disorganization that perturbs the spatial localization of a source. In section (1), disorganization constrains spatial precession, making the source locus smaller and the rhythm more regular. In section (2), disorganization exacerbates source precession, the rotor precesses to another region of the heart, where it may self-terminate or be easier to treat.

FIG. 20 indicates disorganization that perturbs the source to the point of terminating the source of the disorder.

Figure 21:
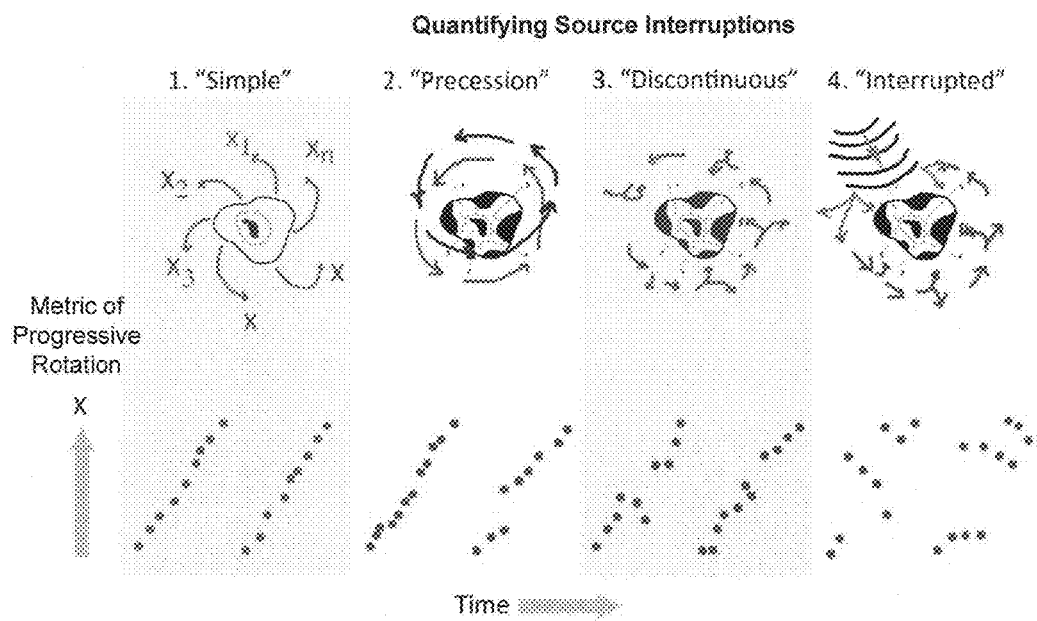
FIG. 21 illustrates mathematical approaches to identify sources through perturbations, and thus to quantify perturbations. (1) Unperturbed source, indicated by linear progressive angular deviation (PAD) correlations of $X_1 \ldots X_n$ for repeated cycles of activation. (2) Precession, with deviations of PADs from the ideal PAD correlations. (3) Discontinuous, where external disorganized activity fuses with peripheral portions of the source. (4) Interrupted, where external disorganized activity eliminates portions of rotation around the source.

FIG. 21 illustrates mathematical approaches to identify sources through perturbations, and thus to quantify perturbations. In section (1), there is illustrated an unperturbed source, indicated by linear progressive angular deviation (PAD) correlations of X1 . . . Xn for repeated cycles of activation. In section (2), there is illustrated source precession, with deviations of PADs from the ideal PAD correlations. In section (3), there is illustrated a discontinuous source, where external disorganized activity fuses with peripheral portions of the source. In section (4), an interrupted source is illustrated, where external disorganized activity eliminates portions of rotation around the source.

Figure 22:
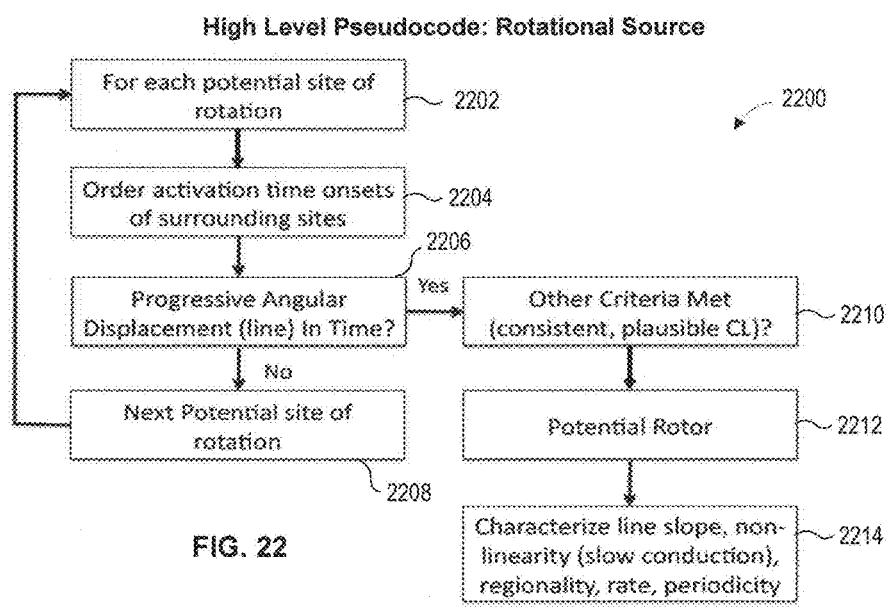
FIG. 22 is an example flowchart associated with characterizing progressive angular deviations (PADs) of a rotational source in relation to a potential site.

FIG. 22 is a flowchart of an example method 2200 of characterizing progressive angular deviations (PADs) of a rotational source in relation to a potential site.

At operation 2202, a potential site related to surrounding sites is selected. At operation 2204, activation onset times of the surrounding sites are ordered. At operation 2206, a determination is made as to whether there is progressive angular deviation in connection with the surrounding sites over an analysis time interval. If so, operations 2210-2214 are performed in connection with the selected potential site. In alternate embodiments, operation 2206 can be substituted with other analyses of focal beats. For example, operation 2206 can use, instead of PAD, progressive vectors, progressive rotational number, progressive correlation, trigonometric function, or another mathematical tool. Operations 2202-2208 are iterated for each of the potential sites.

If there is progressive angular deviation in connection with a potential site, then at operation 2310, a determination is made as to whether other criteria is met, such as consistency in the progressive angular deviations and whether a plausible cycle length is possible in connection with consistent progressive angular deviations. If so, at operation 2212 a potential rotor can be indicated by such consistency and plausible cycle length. At operation 2214, the progressive angular deviations can be characterized by line slope, non-linearity (slow conduction), regionality, rate and periodicity.

Figure 23:
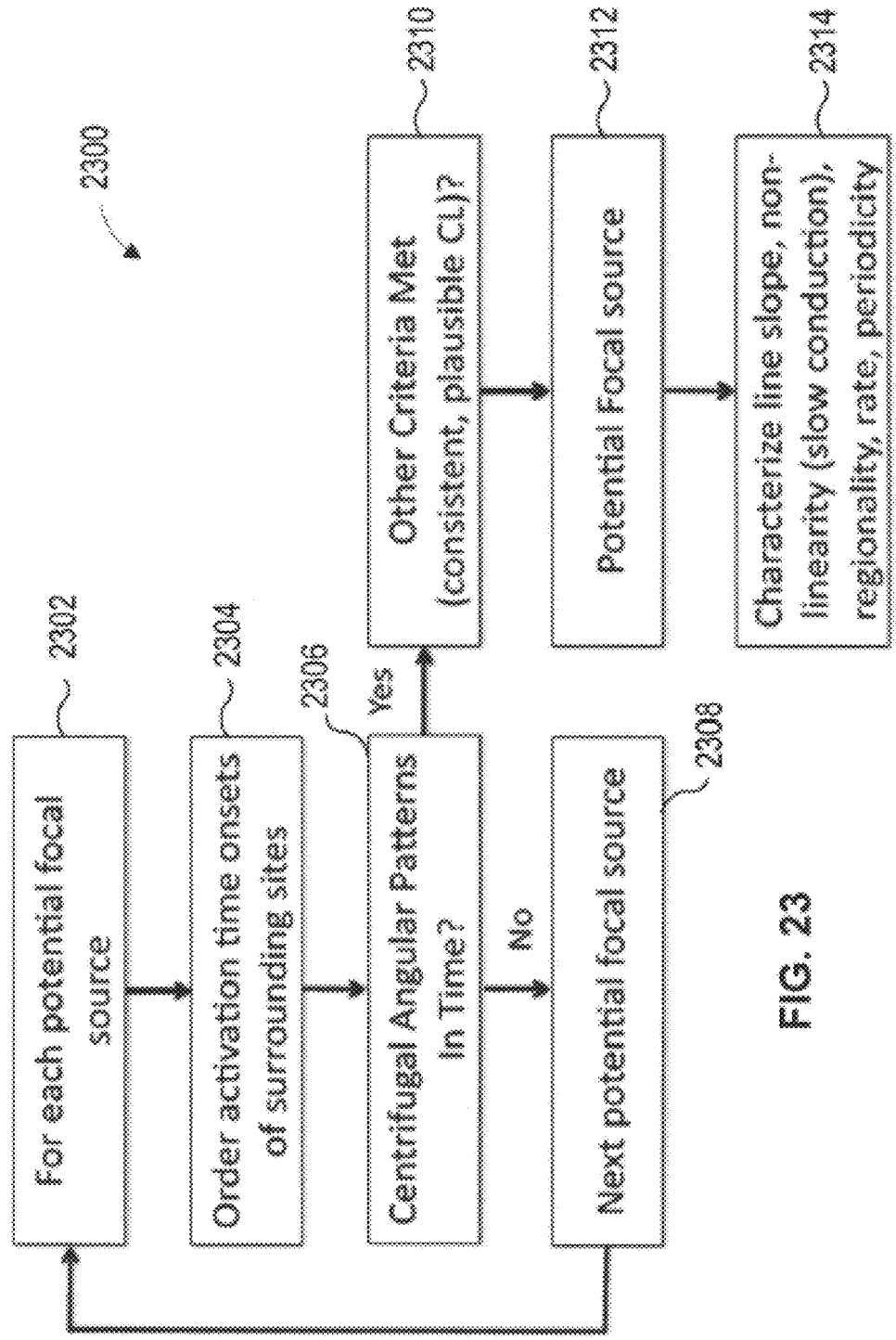
FIG. 23 is an example flowchart associated with characterizing progressive angular deviations (PADs) of a focal source in relation to a potential site.

FIG. 23 is a flowchart of an example method 2300 of characterizing progressive angular deviations (PADs) of a focal source in relation to a potential site.

At operation 2302, a potential site related to surrounding sites is selected. At operation 2304, activation onset times of the surrounding sites are ordered. At operation 2306, a determination is made as to whether there is progressive angular deviation in connection with the surrounding sites over an analysis time interval. If so, operations 2310-2314 are performed in connection with the selected potential site. In alternate embodiments, operation 2306 can be substituted with other analyses of focal beats. For example, operation 2306 can use, instead of PAD, progressive vectors (showing zero sum vector in all directions indicative of focal activation), progressive focal number, progressive correlation, trigonometric function, or another mathematical tool. Operations 2302-2308 are iterated for each of the potential sites.

If there is progressive angular deviation in connection with a potential site, then at operation 2310, a determination is made as to whether other criteria is met, such as consistency in the progressive angular deviations and whether a plausible cycle length is possible in connection with consistent progressive angular deviations. If so, at operation 2312 a potential focal source can be indicated by such consistency and plausible cycle length. At operation 2314, the progressive angular deviations can be characterized by line slope, non-linearity (slow conduction), regionality, rate and periodicity.

Figure 24:
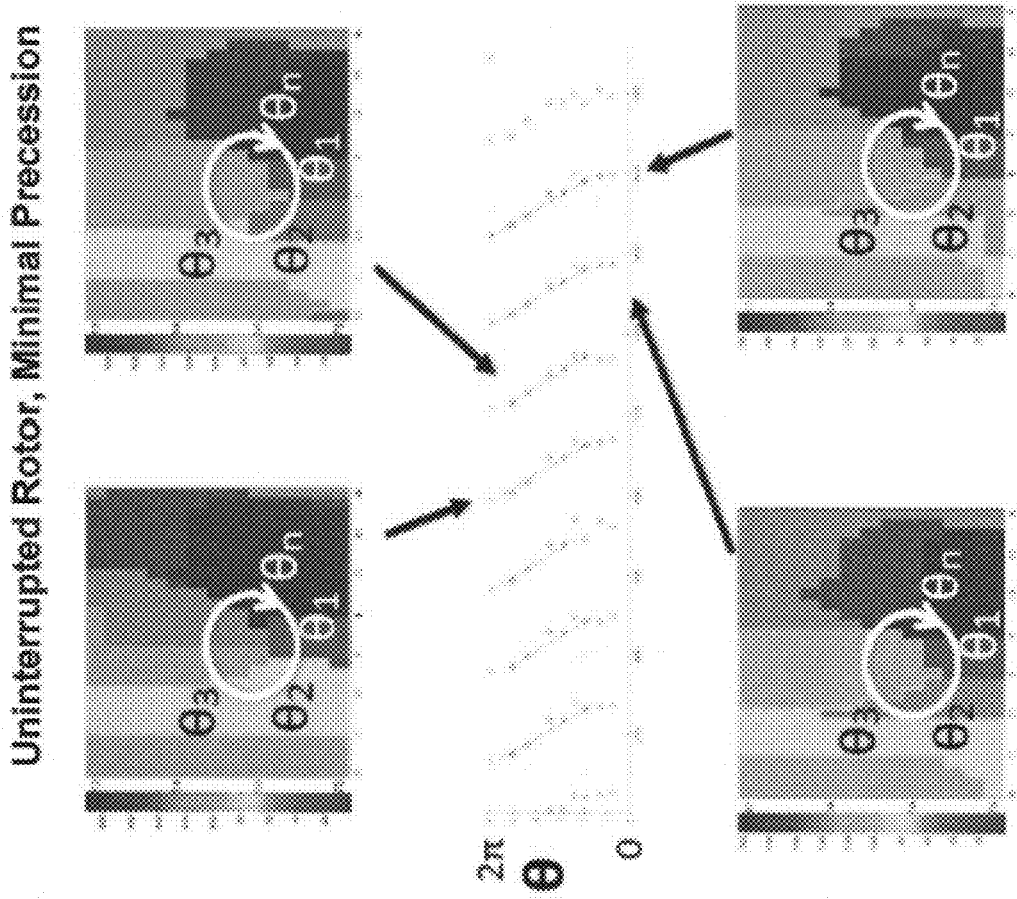
FIG. 24 indicates progressive angular deviations near-ideally correlated (lines of correlation) indicating uninterrupted rotors with minimal precession. Similar results could be obtained using another metric of progressive rotation.

FIG. 24 is a pictorial representation of successive rotations of a rotor during atrial fibrillation in a patient, each of which is consistent from cycle to cycle and is detected by consistent and uninterrupted angular deviations (e.g., angles theta from 0 to 2 pi) from cycle to cycle. It should be noted that this rotation is at the center of a stable source for atrial fibrillation, but could also lie within ventricular fibrillation, or a simple rhythm such as atrial flutter.

Figure 25:
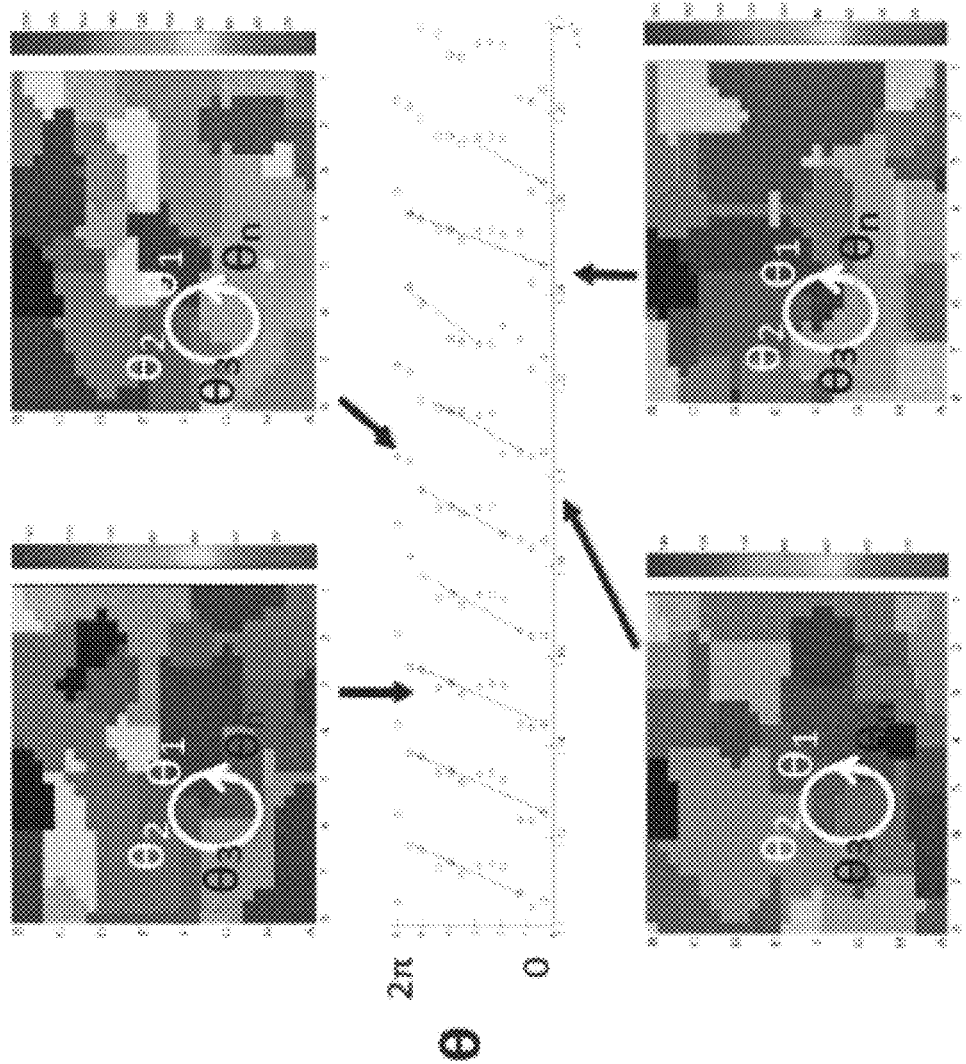
FIG. 25 indicates correlated progressive angular deviations that show rotational activation although the rotor periphery (spiral arms) are interrupted and the rotor core precesses. Similar results could be obtained using another metric of progressive rotation.

FIG. 25 is a pictorial representation of successive rotations of a rotor within a complex rhythm (e.g., atrial fibrillation) in a patient. The rotor is stable but interrupted by activation from outside the rotor, which may indicate fibrillatory conduction or another source. The rotor also precesses (wobbles) showing slight spatial movement but within a stable spatial area. The progressive angular deviation plots show straight lines of theta against time, but with some biological noise reflecting these interruptions.

Figure 26:
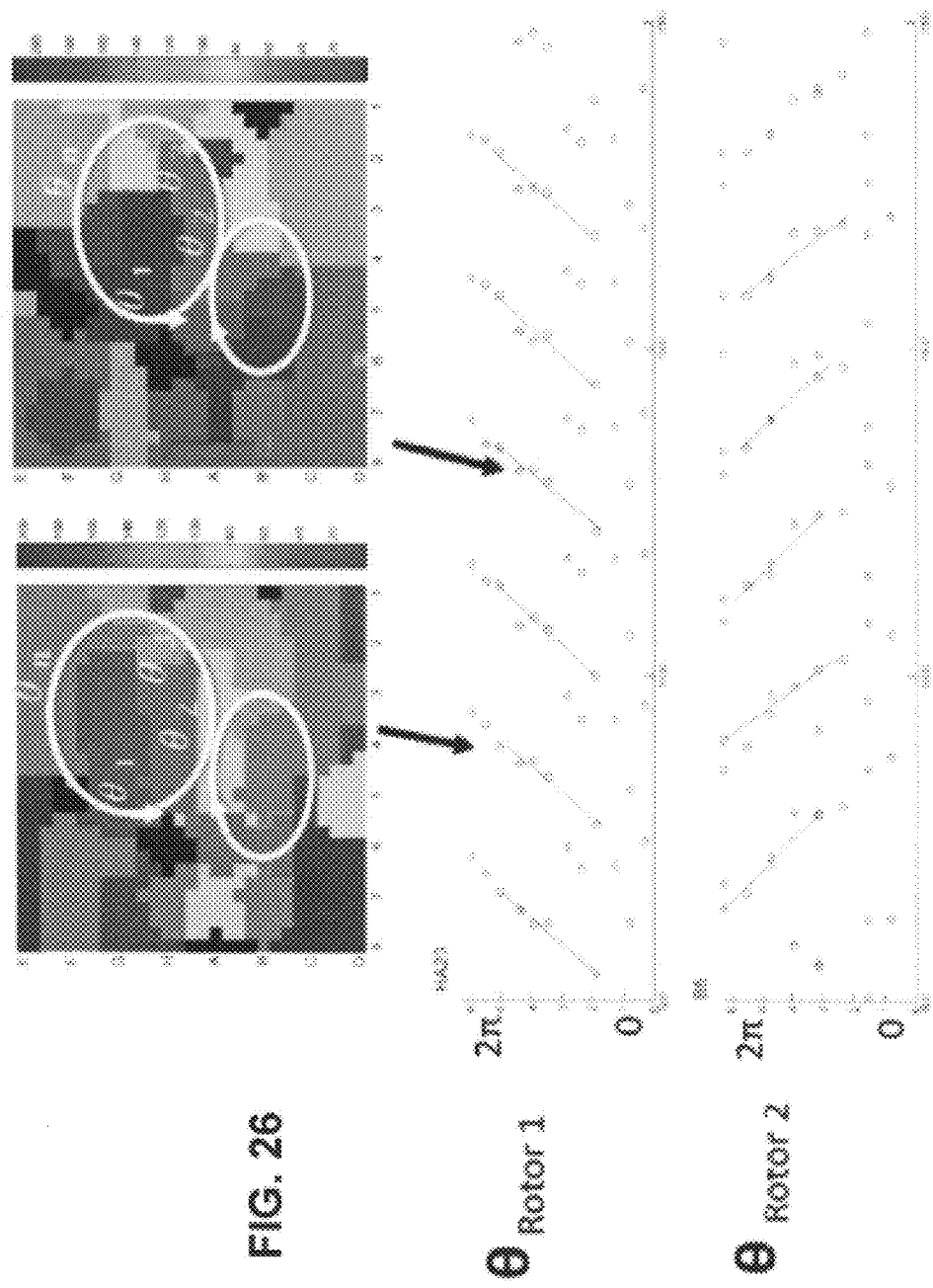
FIG. 26 indicates two concurrent rotors for which correlations of the progressive angular deviations show both rotors (of opposite chirality) despite each interfering with the other Similar results could be obtained using another metric of progressive rotation.

FIG. 26 is a pictorial representation of successive rotations of 2 concurrent rotors in a patient with atrial fibrillation. As illustrated, both rotors are stable with some interruptions by the fibrillatory milieu. Rotor 1 is interrupted more than rotor 2. Both rotors also show slight precession ('wobble'). Accordingly, progressive angular deviation plots show straight lines of theta against time, but with some biological noise reflecting these interruptions.

Figure 27:
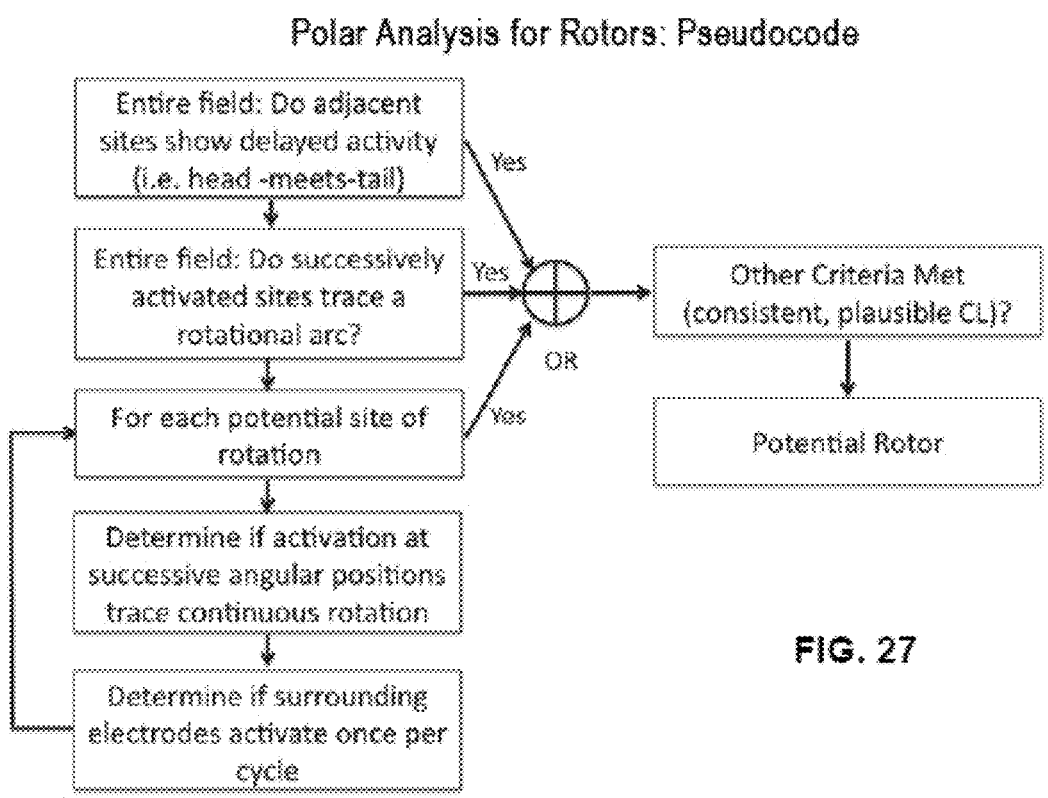
FIG. 27 indicates an example flowchart of the logic for polar analysis of rotations (PAR) for rotational activation trails during a heart rhythm disorder.

FIG. 27 is a flowchart for analyzing a polar analysis of rotations (PAR) for a rotational activation trail using polar analyses. Each operation provides a polar index of rotation, which are combined (or weighted) to determine a rotor. Operation 1 determines activation delay for all adjacent sites for an entire tracing (at least a majority of one complete cycle). In general, conduction time within human atria is 40-200 cm/second, such that activation time delay between electrodes spaced 0.6 cm apart is 3-15 milliseconds (typically 5-10 ms), scaled appropriately for different spacing between electrodes. Conversely, if a rotor is present then activation at adjacent electrodes could be separated by an entire cycle length if they lie at the head versus tail, i.e., activation has to complete a rotation to reach the tail (up to ~200 ms). Operation 2 determines the angular displacement for successively activated sites within the atria. If successively activated sites mostly show the angular deviation expected from a rotation, i.e., 2pi/8 (for 8 surrounding electrodes), then the central electrode is consistent with the core of rotor. Operation 3 examines and determines systematically for all sites in the chamber, if successive surrounding electrodes (in a clock face type of orientation) trace successive angular deviations over time. If so, this is consistent with rotational activation. Operation 4 determines the number of activations at each surrounding electrode per cycle. If this is less than one (1), then dropout (or block into that site) may exist. If this is more than one (1), then double counting or disorganization (fibrillatory conduction) may exist.

Figure 28:
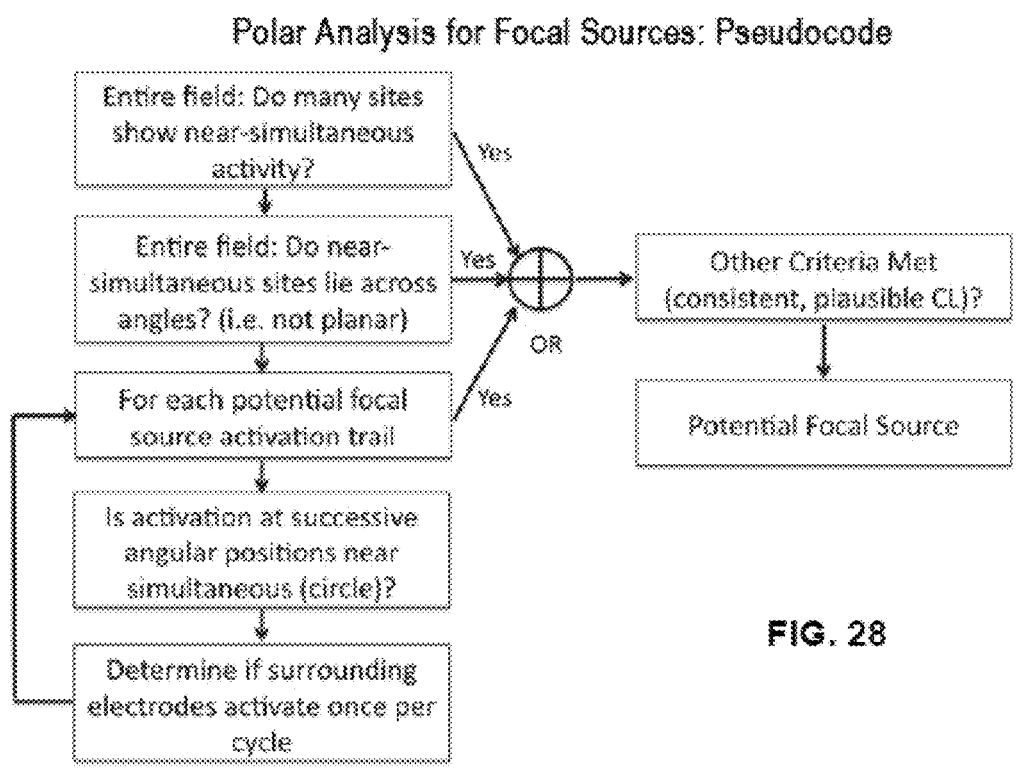
FIG. 28 indicates an example flowchart of the logic for polar analysis of rotations (PAR) for centrifugal activation trails during a heart rhythm disorder.

FIG. 28 is a flowchart of an example method of analyzing a polar analysis of rotations (PAR) for a focal (centrifugal) activation trail. Each operation provides a focal index of rotation, combined (or weighted) equally or non-uniformly to determine a focal source. Operation 1 determines activation delay for all adjacent sites for an entire tracing (at least one complete cycle). In general, conduction time within human atria is 40-200 cm/second, such that activation time delay between electrodes spaced 0.6 cm apart is 3-15 ms (typically 5-10 ms), scaled appropriately for different spacing between electrodes. For a focal source, there will be simultaneous activation of electrodes on concentric circles, unless/until the source disorganizes (fibrillatory conduction). Operation 2 determines angular displacement for successively activated sites within the atria. If successively activated sites mostly show patterns expected from a focal source, then the central electrode is consistent with a focal origin. Operation 3 examines and determines systematically for all sites in the chamber, if successively activated electrodes (in a clock face type of orientation) trace zero angular deviations along each radius from the origin, i.e., centrifugal. Operation 4 determines the number of activations at each surrounding electrode per cycle. If this is less than one (1), then dropout may exist (or block into that site). If this is more than one (1), then double counting or disorganization (fibrillatory conduction) may exist.

Figure 29:
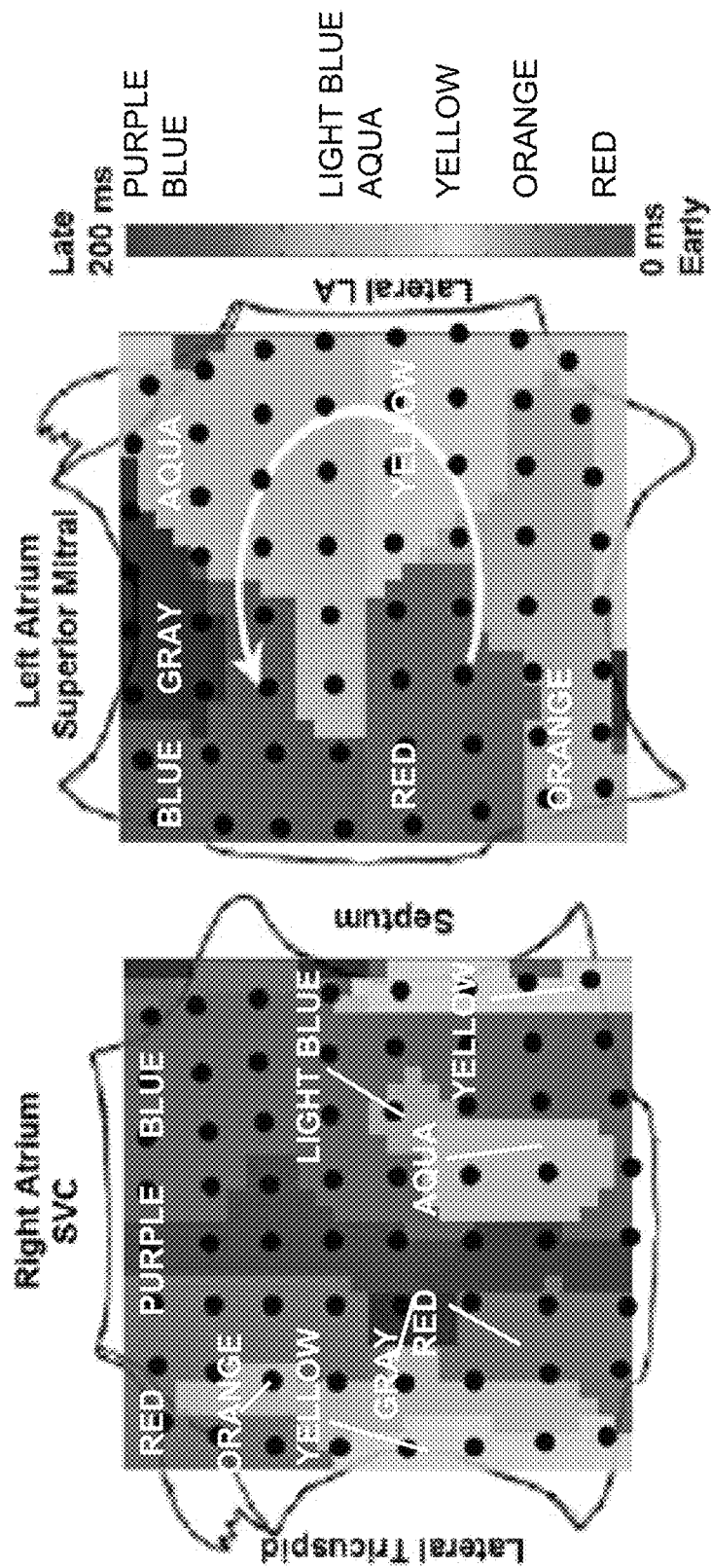
FIG. 29 illustrates a rotor in the left atrium that drives atrial fibrillation, with disorganized activity in the right atrium. The rotor is counterclockwise.

FIG. 29 illustrates a counterclockwise rotor in the left atrium during atrial fibrillation in a patient.

Figure 30:
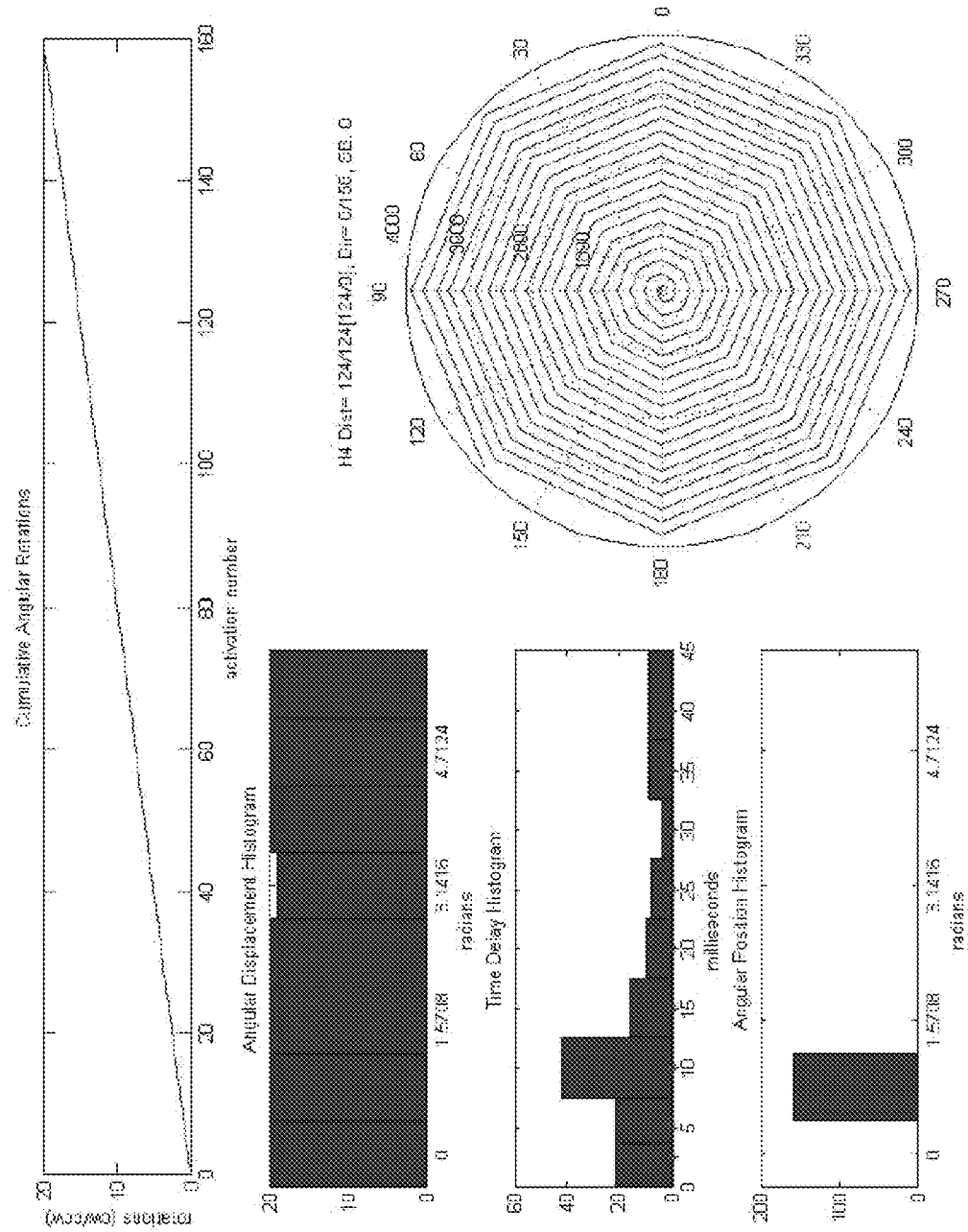
FIG. 30 indicates polar analyses at the core of the rotor in FIG. 29, which indicates polar metrics of rotational activity.

FIG. 30 illustrates detection of the rotor core by polar analysis of rotations (PAR). The inset (right) shows a clear polar spiral line indicating an uninterrupted rotor at the central point (labeled H5 in the spatial plot in FIG. 29). The top graph indicates cumulative angular deviation in number of rotational spins around this central site (vertical axis, 20) for 160 activations at 8 surrounding electrodes (i.e., 20 spins). The top left angular displacement histogram indicates that each angular position around the central core (i.e., all surrounding 8 electrodes) are activated 20 times each (vertical scale), i.e., equally per each location. The electrode with 19 activations indicates possible signal drop out. The middle left time delay histogram shows that many adjacent sites in the entire field activate with delays of 25 ms, 35 ms or 45 ms, far longer than supported by passive conduction. The bottom left angular position histogram shows that all sites (i.e., 160 activations, for 20 activations at 8 sites activated successively in time) are separated by an angular deviation of 2pi/8, i.e., pi/4 radians—the angular deviation between two (2) adjacent electrodes.

Figure 31:
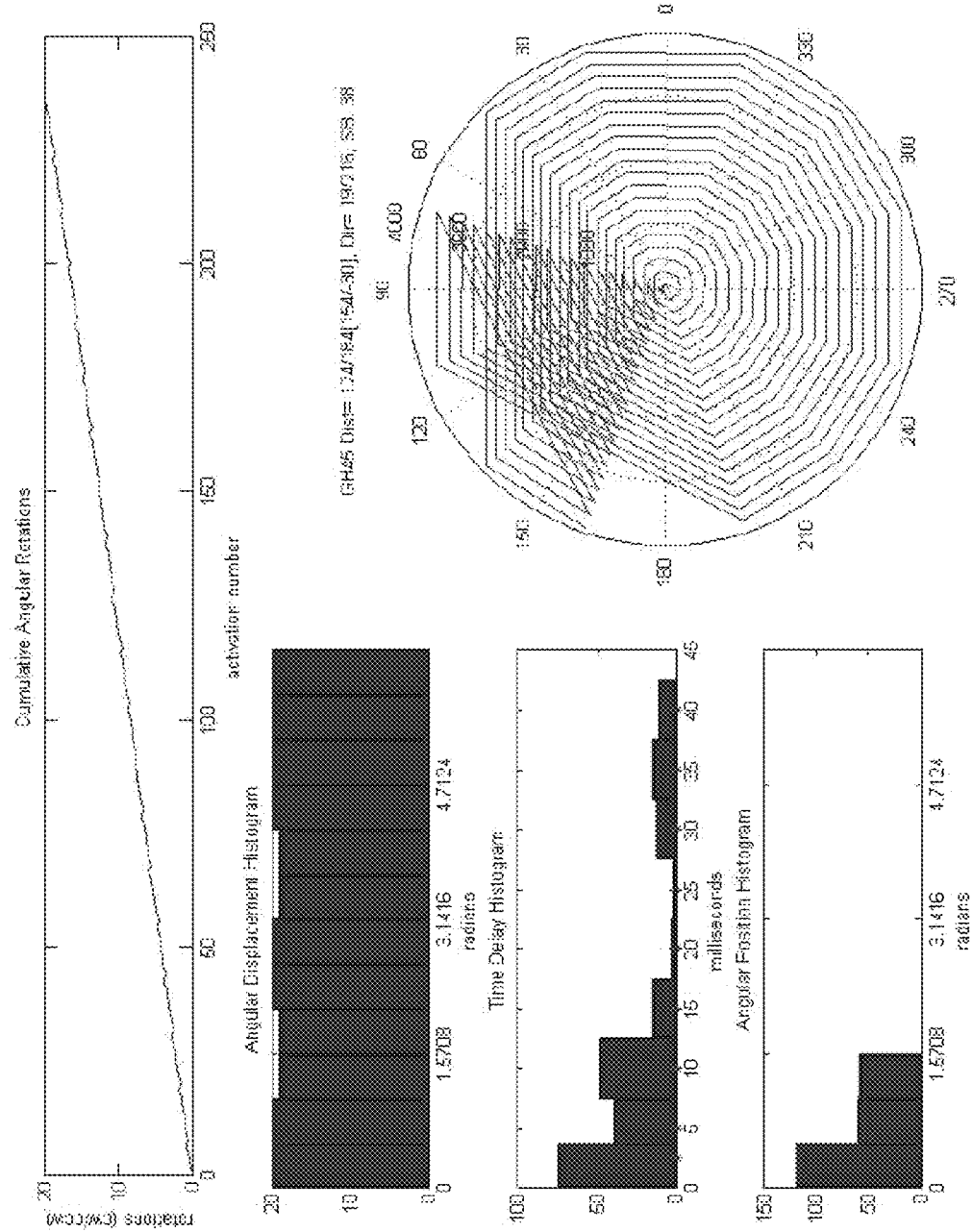
FIG. 31 indicates polar analyses just outside the core of the rotor in FIG. 29, which shows polar metrics indicating partial rotational activity.

FIG. 31 illustrates polar analyses of rotation (PAR) for a site just outside the rotor (GH56). Is should be noted that the raw polar plot shows additional lines that deviate from a spiral, indicating subsidiary (fibrillatory) activation. The top central graph shows complete rotations (vertical scale) over 240 activations at 12 surrounding electrodes (i.e., 20 spins). The top left angular displacement histogram shows that most electrodes (vertical scale) are activated per cycle. The middle left time delay histogram shows the beginning of a bimodal distribution—in that a dominant number of electrodes activate rapidly (i.e., within 5-10 ms), indicating possible passive activation, with some still activating late as expected of rotational activity. The bottom left angular position histogram shows that many sites (vertical scale) activated successively in time are often separated by pi/4, but often by pi/2 radians (i.e., further away—not rotational).

Figure 32:
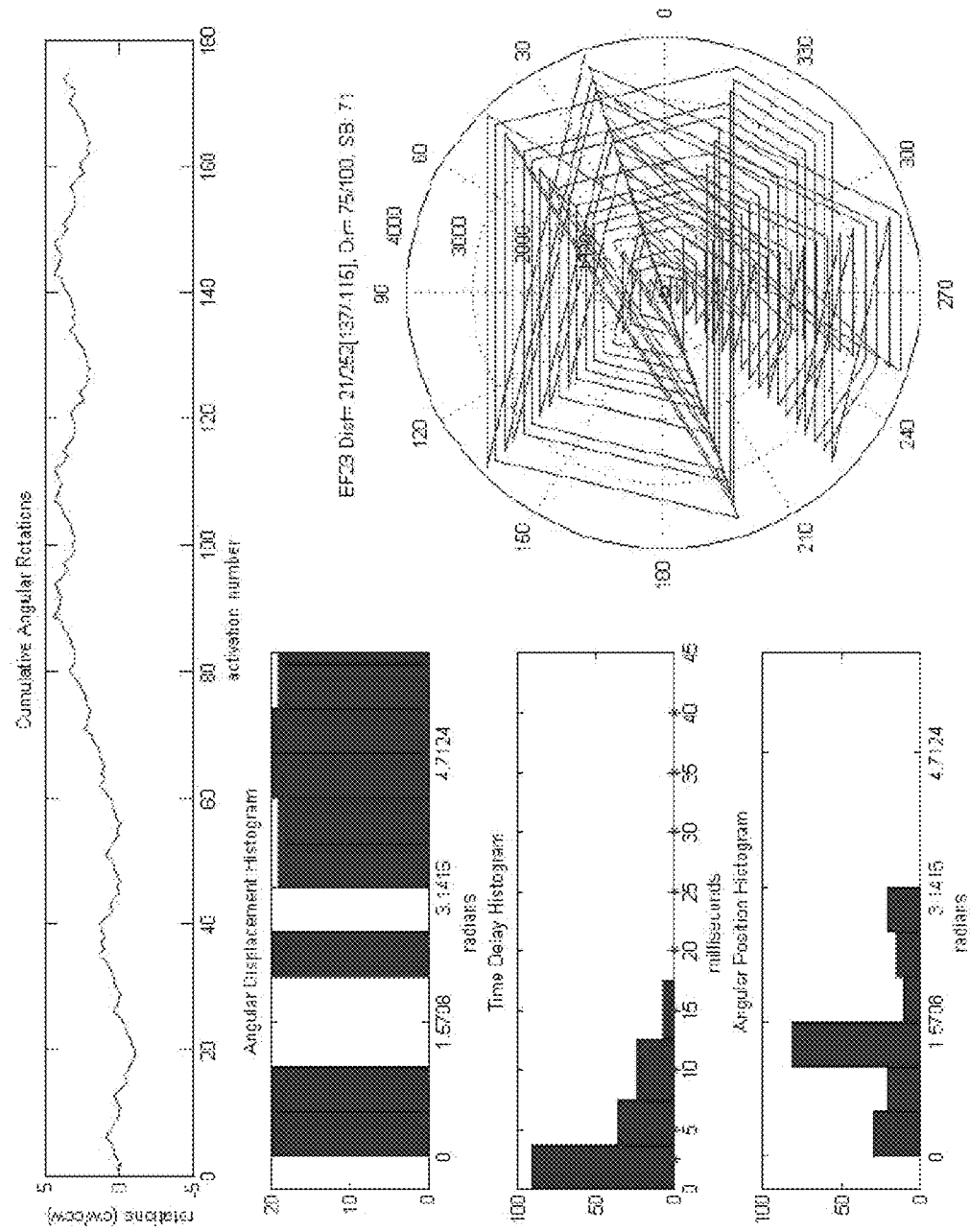
FIG. 32 indicates polar analyses of rotation (PAR) outside the core of the rotor in FIG. 29, which shows polar metrics indicating passive non-rotational activation.

FIG. 32 illustrates polar analysis of rotation (PAR) for a site distant from the rotor (EF23). That raw polar plot shows nearly chaotic activity that does not trace a spiral, which indicates non-rotational activation. The top central graph shows that the cumulative rotational counter does not rise progressively, and actually reverses periodically (falls below zero, i.e., anti-phase). The top left angular displacement histogram shows that many electrodes (vertical scale) are not activated at all, likely indicating signal dropout or regions of block. This metric thus enables one to identify sites—where the organized rotor domain ends and fibrillatory conduction starts. The middle left time delay histogram shows that nearly all electrodes activate rapidly (i.e., within 5-15 ms) indicating passive conduction and inconsistent head-meets-tail rotation. The bottom left angular position histogram shows that sites activated successively in time (vertical scale) are often widely separated in space (i.e., pi/4, pi/2 and even pi radians—i.e., up to 180 degrees separated). This indicates very little or no sequential organization—not rotational.

FIG. 14 is a block diagram of an illustrative embodiment of a general computer system 1400. The computer system 1400 can be the signal processing device 114 and the computing device 116 of FIG. 1. The computer system 1400 can include a set of instructions that can be executed to cause the computer system 1400 to perform any one or more of the methods or computer based functions disclosed herein. The computer system 1400, or any portion thereof, may operate as a standalone device or may be connected, e.g., using a network or other connection, to other computer systems or peripheral devices. For example, the computer system 1400 may be operatively connected to signal processing device 114 and analysis database 118.

In operation as described in FIGS. 1-32, the identification of source(s) of heart rhythm disorders as described herein can be used to identify patients in whom therapy can be effective and to assist in guiding such therapy, which can include delivery of one or more of ablation, electrical energy, mechanical energy, drugs, cells, genes and biological agents to at least a portion of the identified source(s) of the heart.

The computer system 1400 may also be implemented as or incorporated into various devices, such as a personal computer (PC), a tablet PC, a personal digital assistant (PDA), a mobile device, a palmtop computer, a laptop computer, a desktop computer, a communications device, a control system, a web appliance, or any other machine capable of executing a set of instructions (sequentially or otherwise) that specify actions to be taken by that machine. Further, while a single computer system 1400 is illustrated, the term "system" shall also be taken to include any collection of systems or sub-systems that individually or jointly execute a set, or multiple sets, of instructions to perform one or more computer functions.

As illustrated in FIG. 14, the computer system 1400 may include a processor 1402, e.g., a central processing unit (CPU), a graphics-processing unit (GPU), or both. Moreover, the computer system 1400 may include a main memory 1404 and a static memory 1406 that can communicate with each other via a bus 1426. As shown, the computer system 1400 may further include a video display unit 1410, such as a liquid crystal display (LCD), an organic light emitting diode (OLED), a flat panel display, a solid state display, or a cathode ray tube (CRT). Additionally, the computer system 1400 may include an input device 1412, such as a keyboard, and a cursor control device 1414, such as a mouse. The computer system 1400 can also include a disk drive unit 1416, a signal generation device 1422, such as a speaker or remote control, and a network interface device 1408.

In a particular embodiment, as depicted in FIG. 14, the disk drive unit 1416 may include a computer-readable medium 1418 in which one or more sets of instructions 1420, e.g., software, can be embedded. Further, the instructions 1420 may embody one or more of the methods or logic as described herein. In a particular embodiment, the instructions 1420 may reside completely, or at least partially, within the main memory 1404, the static memory 1406, and/or within the processor 1402 during execution by the computer system 1400. The main memory 1404 and the processor 1402 also may include computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments, the methods described herein may be implemented by software programs tangibly embodied in a processor-readable medium and may be executed by a processor. Further, in an exemplary, non-limited embodiment, implementations can include distributed processing, component/object distributed processing, and parallel processing. Alternatively, virtual computer system processing can be constructed to implement one or more of the methods or functionality as described herein.

It is also contemplated that a computer-readable medium includes instructions 820 or receives and executes instructions 1420 responsive to a propagated signal, so that a device connected to a network 1424 can communicate voice, video or data over the network 1424. Further, the instructions 1420 may be transmitted or received over the network 1424 via the network interface device 1408.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, example embodiment, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals, such as a signal communicated over a transmission medium. A digital file attachment to an e-mail or other self-contained information archive or set of archives may be considered a distribution medium that is equivalent to a tangible storage medium. Accordingly, any one or more of a computer-readable medium or a distribution medium and other equivalents and successor media, in which data or instructions may be stored, are included herein.

In accordance with various embodiments, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. The software may also utilize a signal containing computer instructions. A digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein may be stored, are included herein.

Thus, a system and method of identifying a source of a heart rhythm disorder, by identification of rotational of focal activation in relation to one or more spatial elements associated with the source of the heart rhythm disorder, have been described. Although specific example embodiments have been described, it will be evident that various modifications and changes may be made to these embodiments without departing from the broader scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of any of the above-described embodiments, and other embodiments not specifically described herein, may be used and are fully contemplated herein.

The Abstract is provided to comply with 37 C.F.R. § 1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure isnot to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Description of the Embodiments, with each claim standing on its own as a separate example embodiment.

What is claimed is:

1. A method associated with identifying one or more sources of a heart rhythm disorder, the method comprising a computing device:
   selecting a spatial element associated with a region of a heart;
   determining progressive rotational activations or progressive focal activations in relation to the selected spatial element;
   forming a plurality of indexes of successive rotational activations or successive focal activations over time;
   selecting from the plurality of indexes one or more indexes that indicate consistency of the successive rotational activations or successive focal activations;
   generating a representation associated with the successive rotational activations or successive focal activations in relation to a portion of the region of the heart; and
   identifying, using the generated representation, one or more sources associated with the heart rhythm disorder.

2. The method of claim 1, wherein an index of a successive rotational activation is a progressive angular displacement in relation to the selected spatial element.

3. The method of claim 1, wherein an index of a successive focal activation is a progressive angular displacement in relation to the selected spatial element.

4. The method of claim 1, wherein an index of a successive rotational activation is a polar analysis of rotation in relation to the selected spatial element.

5. The method of claim 1, wherein an index of a successive focal activation is a polar analysis of rotation in relation to the selected spatial element.

6. The method of claim 1, wherein the selecting, determining, forming, and selecting are performed for a plurality of regions of the heart.

7. The method of claim 1, wherein a successive rotational activation is measured by progressively increasing or decreasing angular deviation.

8. The method of claim 1, wherein a successive rotational activation is measured in a polar coordinate system.

9. The method of claim 1, wherein a successive rotational activation is measured by progressively increasing or decreasing activation time.

10. The method of claim 1, wherein a successive rotational activation is measured by progressive change in phase.

11. The method of claim 1, wherein a successive rotational activation is measured as periodic activity with one or more superimposed non-periodic components.

12. The method of claim 1, wherein a successive rotational activation is determined using a measure of regularity or a measure of irregularity.

13. The method of claim 1, wherein a successive rotational activation is determined using Shannon entropy, Kolmogorov disorder, or other indexes of disorganization.

14. The method of claim 1, wherein deviations from the successive rotational activations or the successive focal activations represent disorganized breakdown from the one or more sources associated with the heart rhythm disorder.

15. The method of claim 1, wherein activations that are not part of the successive rotational activations are determined by disruption of successive activation times, disruption of polar analysis of rotation, disruption of periodic activations, or disruption of phase of rotations.

16. The method of claim 1, wherein deviations from the successive rotational activations or the successive focal activations associated with the one or more sources of the heart rhythm disorder represent interruptions, the interruptions being associated with a different source from the one or more sources associated with the heart rhythm disorder.

17. The method of claim 16, wherein the interruptions have a repeatable frequency.

18. The method of claim 16, wherein the interruptions have a repeatable spatial.

19. The method of claim 16, wherein a location of the different source of the heart rhythm disorder is indicated by spatial direction from which the interruptions disrupt the successive rotational activations or the successive focal activations.

20. The method of claim 1, wherein selecting from the plurality of indexes is based on a ratio of centrifugal to non-centrifugal activations that exceeds a threshold.

21. The method of claim 1, wherein selecting from the plurality of indexes is based on a ratio of rotating to non-rotating activations that exceeds a threshold.

22. The method of claim 21, wherein the threshold varies with a type of the heart rhythm disorder, being higher for a single source and lower for multiple sources associated with the heart rhythm disorder.

23. The method of claim 21, wherein the threshold varies with a type of the heart rhythm disorder, being higher for simple heart rhythm disorders and lower for complex heart rhythm disorders.

24. The method of claim 1, further comprising refining the determining based upon spatial migration of the one or more sources of the heart rhythm disorder.

25. The method of claim 1, further comprising determining a dominant source from the one or more sources when successive rotational activations or successive focal activations are detected at electrodes with a greater distance from the spatial element relative to neighboring electrodes.

26. The method of claim 1, further comprising delivering treatment to the one or more sources to treat the heart rhythm disorder.

27. The method of claim 26, further comprising delivering treatment to a source from the one or more sources that is dominant in order to treat the heart rhythm disorder.

28. The method of claim 26, further comprising delivering treatment to a source from the one or more sources that is not dominant in order to treat the heart rhythm disorder.

29. The method of claim 1, further comprising delivering treatment to modulate a source from the one or more sources of the heart rhythm disorder.

30. The method of claim 29, wherein the treatment comprises delivering one or more of destructive energy (ablation), therapy based on electroporation, non-destructive energy (pacing), gene therapy, and stem cell therapy.

31. The method of claim 29, wherein modulation is measurable in one of time, space, and combination of time and space.

32. The method of claim 1, wherein the heart rhythm disorder comprises one or more of atrial fibrillation, ventricular fibrillation, atrial tachycardia, atrial flutter, polymorphic or monomorphic ventricular tachycardia, ventricular flutter, and other rhythm disorder within the heart.

33. The method of claim 1, wherein the region of the heart lies in one or more of the heart, nerves that supply regions of the heart, blood vessels that supply regions of the heart, and tissues adjacent to the heart.

34. The method of claim 1, further comprising delivering treatment by modifying the portion of the region.

35. The method of claim 34, wherein modifying comprises destroying the portion.

36. The method of claim 34, wherein modifying the portion comprises delivery to the portion of one or more of ablation, electrical therapy, mechanical therapy, drug therapy, gene therapy, therapy based on electroporation, and stem cell therapy.

37. The method of claim 1, further comprising delivering treatment by selectively modifying one or more parts of the portion.

38. The method of claim 37, wherein modifying comprises destroying the one or more parts.

39. The method of claim 1, wherein the progressive rotational activations or progressive focal activations are angular deviations of activation in relation to the selected spatial element.

40. The method of claim 1, wherein selecting one or more indexes that indicate consistency of the successive rotational activations or the successive focal activations is based on one or more criteria selected from the group consisting of periodicity, slope, linearity, non-linearity, root mean square error (RMSE), cycle length, best-fit analysis, time interval, and combinations thereof.

41. The method of claim 1, further comprising performing selecting, determining, forming, and selecting in connection with additional selected spatial elements to identify consistency of activation in relation to additional portions of the region of the heart.

42. The method of claim 41, further comprising delivering treatment to the one or more of the additional portions of the region of the heart.

43. The method of claim 1, wherein activations that are not part of the successive rotational activations are determined by disruption of progressive angular deviations.

44. A system associated with identifying one or more sources of a heart rhythm disorder, the system comprising:
a processor; and a memory storing instructions that, when executed by the processor, cause the processor to perform operations comprising:

selecting a spatial element associated with a region of a heart;

determining progressive rotational activations or progressive focal activations in relation to the selected spatial element;

forming a plurality of indexes of successive rotational activations or successive focal activations over time;

selecting from the plurality of indexes one or more indexes that indicate consistency of the successive rotational activations or successive focal activations;

generating a representation associated with the successive rotational activations or successive focal activations in relation to a portion of the region of the heart; and identifying, using the generated representation, one or more sources associated with the heart rhythm disorder.

45. A non-transitory storage medium storing instructions that, when executed by the processor, cause the processor to perform operations associated with identifying one or more sources of a heart rhythm disorder, the operations comprising:

selecting a spatial element associated with a region of a heart;

determining progressive rotational activations or progressive focal activations in relation to the selected spatial element;

forming a plurality of indexes of successive rotational activations or successive focal activations over time;

selecting from the plurality of indexes one or more indexes that indicate consistency of the successive rotational activations or successive focal activations;

generating a representation associated with the successive rotational activations or successive focal activations in relation to a portion of the region of the heart; and identifying, using the generated representation, one or more sources associated with the heart rhythm disorder.

* * * * *